United States Patent
Viaud et al.

(10) Patent No.: US 11,357,790 B2
(45) Date of Patent: *Jun. 14, 2022

(54) STERILE FORMULATION COMPRISING A STABLE PHOSPHOROTHIOATE OLIGONUCLEOTIDE

(71) Applicant: GENE SIGNAL INTERNATIONAL SA, Lausanne (CH)

(72) Inventors: Éric Viaud, Lausanne (CH); Antoine Ferry, Paris (FR); Carla Missiaen, Ostend (BE); Jo Vercammen, Sint-Pieters-Leeuw (BE)

(73) Assignee: GENE SIGNAL INTERNATIONAL SA, Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/483,189

(22) PCT Filed: Feb. 2, 2018

(86) PCT No.: PCT/EP2018/052663
§ 371 (c)(1),
(2) Date: Aug. 2, 2019

(87) PCT Pub. No.: WO2018/141908
PCT Pub. Date: Aug. 9, 2018

(65) Prior Publication Data
US 2019/0350963 A1    Nov. 21, 2019

Related U.S. Application Data

(63) Continuation of application No. 15/423,964, filed on Feb. 3, 2017, now Pat. No. 10,052,343.

(30) Foreign Application Priority Data

Feb. 3, 2017   (EP) ..................... 17154670

(51) Int. Cl.
*C07H 21/02* (2006.01)
*C07H 21/04* (2006.01)
*A61K 31/713* (2006.01)
*A61K 47/12* (2006.01)
*A61K 47/02* (2006.01)
*A61K 47/20* (2006.01)
*A61K 9/00* (2006.01)
*A61K 9/107* (2006.01)
*A61K 9/113* (2006.01)
*C12N 15/113* (2010.01)

(52) U.S. Cl.
CPC .......... *A61K 31/713* (2013.01); *A61K 9/0048* (2013.01); *A61K 9/107* (2013.01); *A61K 9/113* (2013.01); *A61K 47/02* (2013.01); *A61K 47/12* (2013.01); *A61K 47/20* (2013.01); *C12N 15/113* (2013.01); *C12N 15/1138* (2013.01); *C12N 2310/11* (2013.01); *C12N 2310/315* (2013.01); *C12N 2320/51* (2013.01)

(58) Field of Classification Search
CPC ............ C12N 2310/11; C12N 31/7115; A61K 31/713
See application file for complete search history.

(56) References Cited

U.S. PATENT DOCUMENTS

| | | | |
|---|---|---|---|
| 2012/0149758 A1 | 6/2012 | Al Mahmood | |
| 2012/0220647 A1* | 8/2012 | Choy | A61K 9/0019 514/44 A |
| 2013/0089513 A1* | 4/2013 | Chung | A61P 25/14 424/85.1 |
| 2014/0328811 A1* | 11/2014 | Wong | C12N 15/113 424/93.21 |
| 2016/0008464 A1* | 1/2016 | Pham | C07K 16/22 424/133.1 |

FOREIGN PATENT DOCUMENTS

| | | | |
|---|---|---|---|
| EP | 3128007 A1 | 2/2017 | |
| WO | 03/005822 A1 | 1/2003 | |
| WO | WO 2013/151999 A1 * | 10/2013 | ......... C12N 2310/11 |
| WO | 2017/025471 A1 | 2/2017 | |

OTHER PUBLICATIONS

Bertrand et al. (Biochemical and Biophysical Research Communications, 296, 2002, 1000-1004).*
Al-Mahmood et al. (The Journal of Pharmacology and Experimental Therapeutics, 329, 2, 496-504).*
Ede et al. (Bioconjugate Chem, 1994, 5, 373-378).*
International Search Report and Written Opinion dated May 2, 2018 in corresponding International Application No. PCT/EP2018/052663; 10 pages.
Claus Cursiefen et al., "Aganirsen Antisense Oligonucleotide Eye Drops Inhibit Keratitis-Induced Corneal Neovascularization and Reduce Need for Transplantation", American Academy of Ophthalmology, vol. 121, No. 9, Sep. 1, 2014, pp. 1683-1692.

* cited by examiner

*Primary Examiner* — Amy H Bowman
(74) *Attorney, Agent, or Firm* — Maier & Maier, PLLC

(57) ABSTRACT

A composition including a phosphorothioate oligonucleotide and at least one fatty acid and/or at least one emulsifying agent, where the composition is sterile and where the composition includes at least one agent including a thiol group and at least one phosphate compound, and the composition can be an ophthalmic composition. The present invention also relates to a method for obtaining the same and to the therapeutic use thereof.

14 Claims, 2 Drawing Sheets
Specification includes a Sequence Listing.

SEQUENCE LISTING

<160> NUMBER OF SEQ ID NOS: 28

<210> SEQ ID NO 1
<211> LENGTH: 150
<212> TYPE: DNA
<213> ORGANISM: Artificial Sequence
<220> FEATURE:
<223> OTHER INFORMATION: IRS-1 antisense

<400> SEQUENCE: 1
tagtactcga ggcgcgccgg gcccccagcc tcgctggccg cgcgcagtac gaagaagcgt      60
ttgtgcatgc tcttgggttt gcgcaggtag cccaccttgc gcacgtccga gaagccatcg     120
ctctccggag ggctcgccat gctgccaccg                                      150

<210> SEQ ID NO 2
<211> LENGTH: 25
<212> TYPE: DNA
<213> ORGANISM: Artificial Sequence
<220> FEATURE:
<223> OTHER INFORMATION: IRS-1 antisense

<400> SEQUENCE: 2
tctccggagg gctcgccatg ctgct                                            25

<210> SEQ ID NO 3
<211> LENGTH: 25
<212> TYPE: DNA
<213> ORGANISM: Artificial Sequence
<220> FEATURE:
<223> OTHER INFORMATION: IRS-1 antisense

<400> SEQUENCE: 3
tatccggagg gctcgccatg ctgct                                            25

<210> SEQ ID NO 4
<211> LENGTH: 24
<212> TYPE: DNA
<213> ORGANISM: Artificial Sequence
<220> FEATURE:
<223> OTHER INFORMATION: IRS-1 antisense

<400> SEQUENCE: 4
tctccggagg gctcgccatg ctgc                                             24

<210> SEQ ID NO 5
<211> LENGTH: 23
<212> TYPE: DNA
<213> ORGANISM: Artificial Sequence
<220> FEATURE:
<223> OTHER INFORMATION: IRS-1 antisense

<400> SEQUENCE: 5
tctccggagg gctcgccatg ctg                                              23

<210> SEQ ID NO 6
<211> LENGTH: 22
<212> TYPE: DNA
<213> ORGANISM: Artificial Sequence
<220> FEATURE:
<223> OTHER INFORMATION: IRS-1 antisense

<400> SEQUENCE: 6
tctccggagg gctcgccatg ct                                               22

```
<210> SEQ ID NO 7
<211> LENGTH: 21
<212> TYPE: DNA
<213> ORGANISM: Artificial Sequence
<220> FEATURE:
<223> OTHER INFORMATION: IRS-1 antisense

<400> SEQUENCE: 7
tctccggagg gctcgccatg c                                               21

<210> SEQ ID NO 8
<211> LENGTH: 20
<212> TYPE: DNA
<213> ORGANISM: Artificial Sequence
<220> FEATURE:
<223> OTHER INFORMATION: IRS-1 antisense

<400> SEQUENCE: 8
tctccggagg gctcgccatg                                                 20

<210> SEQ ID NO 9
<211> LENGTH: 19
<212> TYPE: DNA
<213> ORGANISM: Artificial Sequence
<220> FEATURE:
<223> OTHER INFORMATION: IRS-1 antisense

<400> SEQUENCE: 9
tctccggagg gctcgccat                                                  19

<210> SEQ ID NO 10
<211> LENGTH: 24
<212> TYPE: DNA
<213> ORGANISM: Artificial Sequence
<220> FEATURE:
<223> OTHER INFORMATION: IRS-1 antisense

<400> SEQUENCE: 10
ctccggaggg ctcgccatgc tgct                                            24

<210> SEQ ID NO 11
<211> LENGTH: 23
<212> TYPE: DNA
<213> ORGANISM: Artificial Sequence
<220> FEATURE:
<223> OTHER INFORMATION: IRS-1 antisense

<400> SEQUENCE: 11
tccggagggc tcgccatgct gct                                             23

<210> SEQ ID NO 12
<211> LENGTH: 22
<212> TYPE: DNA
<213> ORGANISM: Artificial Sequence
<220> FEATURE:
<223> OTHER INFORMATION: IRS-1 antisense

<400> SEQUENCE: 12
ccggagggct cgccatgctg ct                                              22

<210> SEQ ID NO 13
<211> LENGTH: 21
<212> TYPE: DNA
<213> ORGANISM: Artificial Sequence
<220> FEATURE:
<223> OTHER INFORMATION: IRS-1 antisense
```

```
<400> SEQUENCE: 13
cggagggctc gccatgctgc t                                              21

<210> SEQ ID NO 14
<211> LENGTH: 20
<212> TYPE: DNA
<213> ORGANISM: Artificial Sequence
<220> FEATURE:
<223> OTHER INFORMATION: IRS-1 antisense

<400> SEQUENCE: 14
ggagggctcg ccatgctgct                                                20

<210> SEQ ID NO 15
<211> LENGTH: 19
<212> TYPE: DNA
<213> ORGANISM: Artificial Sequence
<220> FEATURE:
<223> OTHER INFORMATION: IRS-1 antisense

<400> SEQUENCE: 15
gagggctcgc catgctgct                                                 19

<210> SEQ ID NO 16
<211> LENGTH: 18
<212> TYPE: DNA
<213> ORGANISM: Artificial Sequence
<220> FEATURE:
<223> OTHER INFORMATION: IRS-1 antisense

<400> SEQUENCE: 16
agggctcgcc atgctgct                                                  18

<210> SEQ ID NO 17
<211> LENGTH: 16
<212> TYPE: DNA
<213> ORGANISM: Artificial Sequence
<220> FEATURE:
<223> OTHER INFORMATION: IRS-1 antisense

<400> SEQUENCE: 17
ggctcgccat gctgct                                                    16

<210> SEQ ID NO 18
<211> LENGTH: 15
<212> TYPE: DNA
<213> ORGANISM: Artificial Sequence
<220> FEATURE:
<223> OTHER INFORMATION: IRS-1 antisense

<400> SEQUENCE: 18
gctcgccatg ctgct                                                     15

<210> SEQ ID NO 19
<211> LENGTH: 14
<212> TYPE: DNA
<213> ORGANISM: Artificial Sequence
<220> FEATURE:
<223> OTHER INFORMATION: IRS-1 antisense

<400> SEQUENCE: 19
ctcgccatgc tgct                                                      14

<210> SEQ ID NO 20
<211> LENGTH: 13
```

```
<212> TYPE: DNA
<213> ORGANISM: Artificial Sequence
<220> FEATURE:
<223> OTHER INFORMATION: IRS-1 antisense

<400> SEQUENCE: 20
tcgccatgct gct                                                         13

<210> SEQ ID NO 21
<211> LENGTH: 12
<212> TYPE: DNA
<213> ORGANISM: Artificial Sequence
<220> FEATURE:
<223> OTHER INFORMATION: IRS-1 antisense

<400> SEQUENCE: 21
cgccatgctg ct                                                          12

<210> SEQ ID NO 22
<211> LENGTH: 24
<212> TYPE: DNA
<213> ORGANISM: Artificial Sequence
<220> FEATURE:
<223> OTHER INFORMATION: IRS-1 antisense

<400> SEQUENCE: 22
tatccggagg gctcgccatg ctgc                                             24

<210> SEQ ID NO 23
<211> LENGTH: 23
<212> TYPE: DNA
<213> ORGANISM: Artificial Sequence
<220> FEATURE:
<223> OTHER INFORMATION: IRS-1 antisense

<400> SEQUENCE: 23
tatccggagg gctcgccatg ctg                                              23

<210> SEQ ID NO 24
<211> LENGTH: 22
<212> TYPE: DNA
<213> ORGANISM: Artificial Sequence
<220> FEATURE:
<223> OTHER INFORMATION: IRS-1 antisense

<400> SEQUENCE: 24
tatccggagg gctcgccatg ct                                               22

<210> SEQ ID NO 25
<211> LENGTH: 21
<212> TYPE: DNA
<213> ORGANISM: Artificial Sequence
<220> FEATURE:
<223> OTHER INFORMATION: IRS-1 antisense

<400> SEQUENCE: 25
tatccggagg gctcgccatg c                                                21

<210> SEQ ID NO 26
<211> LENGTH: 20
<212> TYPE: DNA
<213> ORGANISM: Artificial Sequence
<220> FEATURE:
<223> OTHER INFORMATION: IRS-1 antisense

<400> SEQUENCE: 26
```

```
tatccggagg gctcgccatg                                                      20

<210> SEQ ID NO 27
<211> LENGTH: 19
<212> TYPE: DNA
<213> ORGANISM: Artificial Sequence
<220> FEATURE:
<223> OTHER INFORMATION: IRS-1 antisense

<400> SEQUENCE: 27
tatccggagg gctcgccat                                                       19

<210> SEQ ID NO 28
<211> LENGTH: 24
<212> TYPE: DNA
<213> ORGANISM: Artificial Sequence
<220> FEATURE:
<223> OTHER INFORMATION: IRS-1 antisense

<400> SEQUENCE: 28
atccggaggg ctcgccatgc tgct                                                 24
```

STERILE FORMULATION COMPRISING A STABLE PHOSPHOROTHIOATE OLIGONUCLEOTIDE

FIELD

The present invention relates to the therapeutic use of oligonucleotides and aims at solving the problem of the stability of said oligonucleotides in a composition, in particular in a composition comprising at least one fatty acid and/or at least one emulsifying agent. More specifically, the present invention relates to a sterile composition comprising at least one fatty acid and/or at least one emulsifying agent, a phosphorothioate oligonucleotide, at least one agent containing a thiol group and at least one phosphate compound.

BACKGROUND

Oligonucleotides are commonly used as laboratory tools and increasingly used as therapeutic agents. Oligonucleotides are characterized by their specificity, as they are able to recognize and bind to a specific target, for example through sequence complementarity by virtue of Watson-Crick base pairing. Antisense oligonucleotides, siRNAs and shRNAs, the most common oligonucleotides with therapeutic purposes, are thus able to modulate the expression of a target gene. In particular, antisense oligonucleotides bind to a specific mRNA target and induce its degradation through the recruitment of RNase H, a ubiquitous enzyme that hydrolyzes the RNA strand of RNA/DNA hybrids. Alternatively, some antisense oligonucleotides may act as "steric blockers" as they block the access of cellular machinery to their RNA target. Antisense oligonucleotides are useful in the treatment of many disorders, including cancer, metabolic diseases, inflammatory diseases and angiogenesis related diseases.

Treatments consisting in the administration of an oligonucleotide to a human subject require compositions in which the oligonucleotide is stable. Unmodified oligonucleotides are susceptible to degradation by both intracellular and extracellular nucleases. Chemical modifications of the natural phosphodiester backbone were thus developed, and are currently commonly used to increase the stability of the modified oligonucleotides. In particular, phosphorothioate oligonucleotides are known to be more resistant to degradation by nucleases. Phosphorothioate antisense oligonucleotides are able to activate RNase H activity and thus can induce the degradation of their target mRNA.

Depending on the disease to be treated, different ways of administration and correspondingly different types of composition are used. Phosphorothioate oligonucleotides are very stable in aqueous solutions. However, administration of oligonucleotides has also been envisaged in the form of emulsions, creams or any bi- or multiphasic formulations, in particular for topical administration, in order to ensure a sufficient exposure of the target tissue to the active oligonucleotides. For example, a topical application of an emulsion may be required for the treatment of some diseases of the eyes. Being applied in an emulsion rather than in an aqueous solution may indeed prevent the hydrophilic oligonucleotides from being readily absorbed in the vitreous humor.

However, stability issues arise with phosphorothioate nucleotides in emulsions. Indeed, phosphorothioate oligonucleotides are susceptible to desulfurization through the action of peroxide radicals generated from excipients present in the compositions. WO03005822 presents how the addition of antioxidants which partition into the aqueous phase of a bi- or multiphasic topical formulation prevents desulfurization of phosphorothioate internucleoside linkages.

It should however be noted that the bi- or multiphasic compositions comprising a phosphorothioate oligonucleotide and an antioxidant described in WO03005822 were not submitted to temperatures higher than 40° C. However, some treatments, such as an ophthalmic application, require the administration of a sterile emulsion obtained by autoclaving, i.e., a sterile emulsion obtained by sterilization by saturated steam under pressure (more than 100° C.). Upon autoclaving, the Applicant demonstrated that phosphorothioate oligonucleotides may be subjected to β-elimination following sequential peripheral oxidation, as shown in FIGS. 1 and 2. Without willing to be bound to a theory, the Applicant suggests that exposition of fatty acids and/or emulsifying agents of the emulsion to high temperatures generates highly reactive chemical entities and/or free radicals which could lead to the degradation of the phosphorothioate oligonucleotide.

Thus, there is still a need for a sterile composition comprising at least one fatty acid and/or at least one emulsifying agent wherein the phosphorothioate oligonucleotide is stable.

SUMMARY

The present invention relates to a composition comprising a phosphorothioate oligonucleotide and at least one fatty acid and/or at least one emulsifying agent, wherein said composition is sterile and wherein said composition further comprises at least one phosphate compound and at least one agent comprising a thiol group, preferably said composition is an ophthalmic composition.

In one embodiment, the composition is an emulsion, preferably an oil-in-water emulsion or a water-in-oil-in-water emulsion.

In one embodiment, the agent comprising a thiol group is selected from the group comprising N-acetylcysteine, lipoic acid, DL-cysteine, creatinine, glutathione, 2-mercapto-5-benzimidazole salts, 2-mercaptoethanesulfonic acid salts, Na-edetate, Na-bisulfite and Na-sulfite, preferably the agent comprising a thiol group is lipoic acid, DL-cysteine or N-acetylcysteine.

In one embodiment, the agent comprising a thiol group is selected from the group comprising N-acetylcysteine, lipoic acid, DL-cysteine, creatinine, glutathione, 2-mercapto-5-benzimidazole salts and 2-mercaptoethanesulfonic acid salts, preferably the agent comprising a thiol group is lipoic acid, DL-cysteine or N-acetylcysteine.

In one embodiment, the phosphate compound is selected from the group comprising $Na_2HPO_4$, $NaH_2PO_4$, $Na_3PO_4$, $K_2HPO_4$, $K_3PO_4$, $KH_2PO_4$, $(NH_4)_2HPO_4$, $(NH_4)_3PO_4$, $Mg(H_2PO_4)_2$, $Mg_3(PO_4)_2$, $MgHPO_4$, $MgNH_4PO_4$, $Ca(H_2PO_4)_2$, $CaHPO_4$, $Ca_3(PO_4)_2$, $Ca_8(HPO_4)_2(PO_4)_4$, $H_3PO_4$ and phosphate acid/base conjugate pairs selected from the group comprising $NaH_2PO_4/Na_2HPO_4$, $KH_2PO_4/K_2HPO_4$, $Na_2HPO_4/Na_3PO_4$, and $K_2HPO_4/K_3PO_4$.

In one embodiment, the phosphorothioate oligonucleotide is selected from the group comprising antisense oligonucleotides, siRNAs, shRNAs, ribozymes, aptamers, molecular decoys and RNA-DNA hybrid molecules, preferably said phosphorothioate oligonucleotide is an antisense oligonucleotide.

In one embodiment, the phosphorothioate oligonucleotide is an antisense oligonucleotide specific for IRS-1 (insulin receptor substrate-1), preferably the IRS-1 antisense phosphorothioate oligonucleotide comprises a sequence of at least 12 contiguous nucleotides of SEQ ID NO: 1, more preferably the IRS-1 antisense phosphorothioate oligonucleotide is SEQ ID NO: 2 or a function-conservative derivative thereof.

In one embodiment, the function-conservative derivative of SEQ ID NO: 2 comprises from 9 to 50 nucleotides, has at least about 75% identity compared to SEQ ID NO: 2 and conserves the capacity of inhibiting IRS-1 expression as SEQ ID NO: 2, preferably said function-conservative derivative of SEQ ID NO: 2 is selected from SEQ ID NO: 3 to SEQ ID NO: 28.

In one embodiment, the phosphorothioate oligonucleotide is stable for at least 1 day at 25° C., and/or the phosphorothioate oligonucleotide is stable for at least 1 day at 40° C.

The present invention further relates to a pharmaceutical composition comprising the composition of the invention and at least one pharmaceutically acceptable excipient.

The present invention further relates to a medicament comprising the composition of the invention.

The present invention further relates to a method for preventing and/or inhibiting the degradation of a phosphorothioate oligonucleotide in a composition comprising at least one fatty acid and/or at least one emulsifying agent and subjected to autoclaving, wherein said method comprises adding at least one phosphate compound and/or at least one agent comprising a thiol group within the composition.

The present invention further relates to a method for obtaining a sterile composition comprising a phosphorothioate oligonucleotide and at least one fatty acid and/or at least one emulsifying agent, wherein said phosphorothioate oligonucleotide is stable within the sterile composition, and wherein said method comprises adding at least one phosphate compound and/or at least one agent comprising a thiol group within the composition.

In one embodiment, the method comprises the steps of:
preparing a bulk emulsion, comprising at least one fatty acid and/or at least one emulsifying agent;
sterilizing said bulk emulsion by autoclaving; and
adding a phosphorothioate oligonucleotide, at least one phosphate compound and/or at least one agent comprising a thiol group within the sterile bulk emulsion.

In one embodiment, the percentage of the bulk emulsion ranges from about 60% to about 99% in weight to the total weight of the sterile composition and comprises:
an oil phase, comprising an oil, an emulsifying agent, a thickening agent, and/or an osmolality modifying agent; and
an aqueous phase comprising a viscosity modifying agent, a pH buffering agent, and/or urea; and
the percentage of the phosphorothioate solution ranges from about 1% to about 40% in weight to the total weight of the sterile composition and comprises a phosphorothioate oligonucleotide, at least one phosphate compound and/or at least one agent comprising a thiol group.

The present invention further relates to a composition, pharmaceutical composition or medicament as described hereinabove, wherein the phosphorothioate oligonucleotide is an IRS-1 antisense, for treating an angiogenic disorder.

The present invention further relates to a kit comprising:
a bulk emulsion, comprising at least one fatty acid and/or at least one emulsifying agent;
a phosphorothioate solution, comprising at least one phosphate compound and/or at least one agent comprising a thiol group; and
optionally, a phosphorothioate oligonucleotide.

BRIEF DESCRIPTION OF THE DRAWINGS

FIG. 3A reports the percentage assay results of various formulations of the GS-101 sterile emulsion, incubated at 5° C.; FIG. 3B reports the same results for emulsions incubated at 25° C.; FIG. 3C reports the same results for emulsions incubated at 40° C.

DETAILED DESCRIPTION

Figure 1:
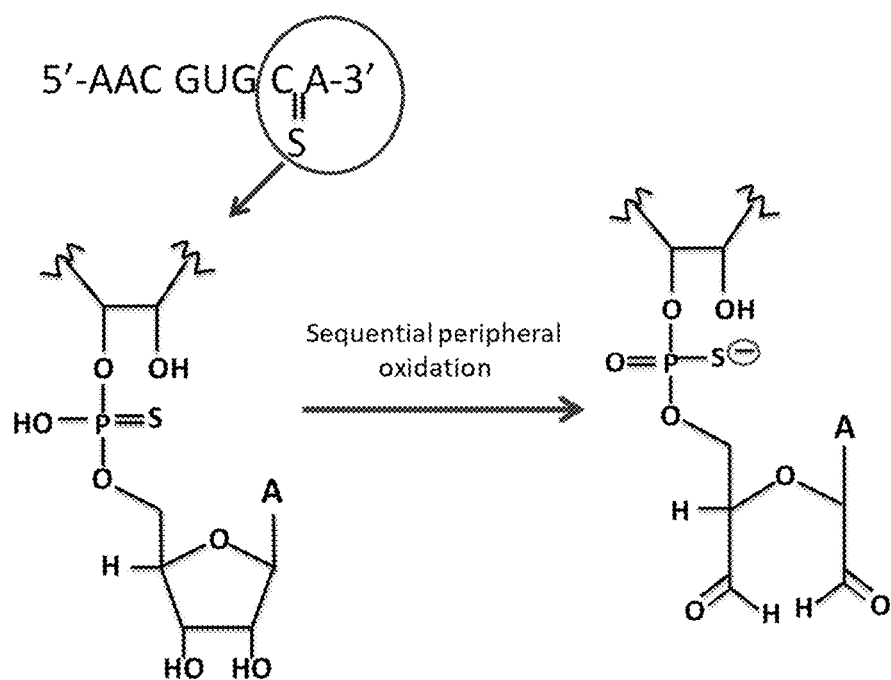
FIG. 1 is a scheme showing the sequential peripheral oxidation of phosphorothioate-derived oligonucleotides.

In the present invention, the following terms have the following meanings:

"Ophthalmic composition": refers to sterile liquid, semi-solid or solid preparations intended for administration upon the eyeball and/or to the conjunctiva, or for insertion in the conjunctival sac or for administration into the posterior segment of the eye. As used herein, the term "posterior segment of the eye" refers to the back two third of the eye, comprising the anterior hyaloids membrane and the structures behind it (vitreous humor, retina, choroid, optic nerve). In particular, an ophthalmic composition may be topically administered or administered into the vitreous humor, for example by intravitreal injection. Examples of ophthalmic compositions include, but are not limited to, eye drops, eye lotions, powders for eye drops and powders for eye lotions, and compositions to be injected into the conjunctival sac or into the vitreous humor.

"Eye drops" refers to sterile aqueous or oily solutions, emulsions or suspensions of one or more active substances intended for instillation into the eye. According to the present invention, the one or more active substances comprises at least one phosphorothioate oligonucleotide.

"Eye lotions" refers to sterile aqueous or oily solutions intended for use in rinsing or bathing the eye or for impregnating eye dressings.

"Oligonucleotide" refers to a nucleic acid molecule, i. e., a polymer of ribonucleic acids and/or deoxyribonucleic acids (the nucleic acid molecule may thus be a DNA and/or a RNA molecule), either single- or double-stranded. In one embodiment, the length of an oligonucleotide ranges from about 5 to about 200 nucleotides, preferably from about 7 to 100 nucleotides, more preferably from 10 to 70 nucleotides and even more preferably from 12 to 30 nucleotides.

"Phosphorothioate oligonucleotide" refers to an oligonucleotide in which at least one non-bridging oxygen on the phosphate backbone of the nucleotides has been replaced by a sulfur atom to form phosphorothioate internucleoside linkages (instead of the natural phosphodiester internucleoside linkages). Such chemical modification protects oligonucleotides from degradation by nucleases, both intracellular and extracellular. Phosphorothioate linkages have also been reported to increase the cellular uptake of the oligonucleotides. They can also bind to serum proteins, slowing excretion by the kidneys.

"Fatty acid" refers to a carboxylic acid with a long aliphatic tail (chain), such as, for example, from 4 to 36 atoms of carbon, which is either saturated or unsaturated.

"Thiol" refers to a group —SH.

"Phosphate compound" refers to a chemical compound bearing at least one —PO$_4$ moiety.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

"About" preceding a figure means plus or minus 10% of the value of said figure.

"Therapeutically effective amount" means level or amount of agent that is aimed at, without causing significant negative or adverse side effects to the target, (1) delaying or preventing the targeted disease, disorder, or condition; (2) slowing down or stopping the progression, aggravation, or deterioration of one or more symptoms of the targeted disease, disorder, or condition; (3) bringing about ameliorations of the symptoms of the targeted disease, disorder, or condition; (4) reducing the severity or incidence of the targeted disease, disorder, or condition; or (5) curing the targeted disease, disorder, or condition. A therapeutically effective amount may be administered prior to the onset of the targeted disease, disorder, or condition, for a prophylactic or preventive action. Alternatively or additionally, the therapeutically effective amount may be administered after initiation of the targeted disease, disorder, or condition, for a therapeutic action.

"Treating" or "treatment" refers to both therapeutic treatment and prophylactic or preventative measures; wherein the object is to prevent or slow down (lessen) the targeted disease, disorder, or condition. Those in need of treatment include those already with the disorder as well as those prone to have the disorder or those in whom the disorder is to be prevented. A subject or mammal is successfully "treated" for a disease or condition if, after receiving a therapeutic amount of a composition according to the present invention, the subject of mammal shows observable and/or measurable improvement of one or more of the following: reduction in the number of pathogenic cells; reduction in the percent of total cells that are pathogenic; and/or relief to some extents, of one or more of the symptoms associated with the specific disease or condition; reduced morbidity and mortality; and/or improvement in quality of life issues. The above parameters for assessing successful treatment and improvement in the disease are readily measurable by routine procedures familiar to a physician.

"Subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease.

DETAILED DESCRIPTION

One object of the invention is a composition comprising a phosphorothioate oligonucleotide and at least one fatty acid and/or at least one emulsifying agent, wherein said composition is sterile and wherein said composition comprises at least one agent comprising a thiol group and at least one phosphate compound.

In one embodiment, the composition of the invention is an ophthalmic composition.

According to the invention, the composition of the invention provides stability to the phosphorothioate oligonucleotide. Without willing to be bound to any theory, the Applicant suggests that the presence of an agent comprising a thiol group prevents the degradation of the phosphorothioate oligonucleotide, while the presence of a phosphate compound stabilizes the structural conformation of the phosphorothioate oligonucleotide. In particular, the presence of an agent comprising a thiol group may prevent the oligonucleotide from attack by chemical bases liberated from fatty acids and/or from emulsifying agents during an autoclaving step.

Examples of compositions comprising at least one fatty acid and/or at least one emulsifying agent include, but are not limited to, gels, ointments, micelles and emulsions.

In one embodiment of the invention, the composition comprising at least one fatty acid and/or at least one emulsifying agent is an emulsion such as a water-in-oil emulsion, an oil-in-water emulsion, a water-in-oil-in-water emulsion or any multiphasic emulsion. Preferably, the composition comprising at least one fatty acid and/or at least one emulsifying agent is a water-in-oil-in-water emulsion, i.e., an oil-in-water emulsion further comprising an aqueous phase inside the oil droplets dispersed in the aqueous phase.

In one embodiment, the emulsion is cationic. In another embodiment, the emulsion is anionic.

In one embodiment, the emulsion of the invention comprises an aqueous phase and an oil phase dispersed in the aqueous phase, wherein:
 the percentage of the aqueous phase ranges from about 70 to about 99% in weight to the total weight of the emulsion, preferably from about 75% to about 85% w/w, more preferably is of about 81.5% w/w; and wherein
 the percentage of the oil phase ranges from about 1 to about 30% in weight to the total weight of the emulsion, preferably from about 10 to about 20% w/w or from about 15 to about 25% w/w, more preferably is of about 18.5% w/w.

In one embodiment, the emulsion of the invention comprises an aqueous phase and an oil phase dispersed in the aqueous phase, wherein:
 the percentage of the aqueous phase ranges from about 70 to about 99% in weight to the total weight of the emulsion, preferably from about 80% to about 90% w/w, more preferably is of about 86.5% w/w; and wherein
 the percentage of the oil phase ranges from about 1 to about 30% in weight to the total weight of the emulsion, preferably from about 10 to about 20% w/w, more preferably is of about 13.5% w/w.

In one embodiment of the invention, the phosphorothioate oligonucleotide is present in the aqueous phase of the emulsion. In one embodiment, the emulsion is a water-in-oil-in-water emulsion, and the phosphorothioate oligonucleotide is present both in the aqueous phase surrounding the oil droplets and in the aqueous phase inside the oil droplets.

In one embodiment of the invention, the at least one agent comprising a thiol group is present in the aqueous phase of the emulsion. In one embodiment, the emulsion is a water-in-oil-in-water emulsion, and the at least one agent comprising a thiol group is present both in the aqueous phase surrounding the oil droplets and in the aqueous phase inside the oil droplets.

In one embodiment of the invention, the at least one phosphate compound is present in the aqueous phase of the emulsion. In one embodiment, the emulsion is a water-in-oil-in-water emulsion, and the at least one phosphate compound is present both in the aqueous phase surrounding the oil droplets and in the aqueous phase inside the oil droplets.

In one embodiment, the phosphorothioate oligonucleotide is an active oligonucleotide that may be used for therapeutic purposes.

In one embodiment, at least one (such as, for example, 1, 2, 3, 4, 5, 6, 7, 8, 9 or 10 or more) phosphodiester linkage of the oligonucleotide of the invention is replaced by a phosphorothioate linkage. In another embodiment, the first phosphodiester linkage in 5' and the first phosphodiester linkage in 3' of the oligonucleotide of the invention are replaced by a phosphorothioate linkage. Preferably, all phosphodiester linkages of the oligonucleotide of the invention are replaced by phosphorothioate linkages.

Examples of phosphorothioate oligonucleotides include, but are not limited to, antisense oligonucleotides, small interfering RNAs (siRNAs), small hairpin RNAs (shRNAs), ribozymes, aptamers, molecular decoys and RNA-DNA hybrid molecules.

Antisense oligonucleotides are commonly used to modulate gene expression through their hybridization to a specific RNA target by virtue of Watson-Crick base pairing. In particular, antisense oligonucleotides bind to a specific mRNA target and may induce its degradation through the recruitment of RNase H, a ubiquitous enzyme that hydrolyzes the RNA strand of RNA/DNA hybrids. Alternatively, some antisense oligonucleotides act as "steric blockers" as they block the access of cellular machinery to their RNA target.

Both siRNAs and shRNAs are able to modulate gene expression through the gene silencing mechanism known as RNA interference in which a small RNA duplex associates with the RNA-induced silencing complex (RISC) to lead the RISC to a specific target mRNA. siRNAs are small double-stranded RNA molecules directly delivered to the cells while shRNAs are artificial RNA molecules with a tight hairpin turn usually delivered to the cells via a plasmid or a vector and further processed within the cells.

Ribozymes are RNA molecules capable of catalyzing specific biochemical reactions. Artificial ribozymes have been designed, for example, to target the RNA of specific viruses.

Aptamers are short synthetic single-stranded oligonucleotides that specifically bind to various molecular targets such as small molecules, proteins, nucleic acids, and even cells and tissues via a mechanism other than Watson-Crick base-pairing. They are essentially a chemical equivalent of antibodies.

Molecular decoys are short double-stranded synthetic polynucleotides with high affinity for a regulatory protein, such as a transcription factor, that can be used to compete with the natural nucleic acid and attenuate the effects of the regulatory protein.

RNA-DNA hybrid molecules, also known as chimeric oligonucleotides (chimeras), have been shown to alter or repair single bases in plant and animal genomes.

In one embodiment of the invention, the bioactive phosphorothioate oligonucleotide is a phosphorothioate antisense oligonucleotide.

In one embodiment of the invention, the phosphorothioate antisense oligonucleotide inhibits the expression of IRS-1 (insulin receptor substrate-1).

In one embodiment of the invention, the IRS-1 antisense oligonucleotide is a sequence of at least 12 nucleotides, preferably at least 12 contiguous oligonucleotides of SEQ ID NO: 1:

```
5'-TAGTACTCGAGGCGCGCCGGGCCCCCAGCCTCGCTGGCCGCGC

GCAGTACGAAGAAGCGTTTGTGCATGCTCTTGGGTTTGCGCAGGTA

GCCCACCTTGCGCACGTCCGAGAAGCCATCGCTCTCCGGAGGGCTC

GCCATGCTGCCACCG-3'.
```

In one embodiment of the invention, the IRS-1 antisense oligonucleotide is a sequence comprising or consisting of at least 12 contiguous nucleotides of SEQ ID NO: 1, preferably at least 13, 14, 15, 16, 17, 18, 19, 20, 21, 22, 23, 24, 25, 26, 27, 28, 29, 30 contiguous nucleotides of SEQ ID NO: 1.

In one embodiment of the invention, the IRS-1 antisense oligonucleotide is a sequence comprising or consisting of at least 12 contiguous nucleotides of SEQ ID NO: 1, preferably at least 13, 14, 15, 16, 17, 18, 19, 20, 21, 22, 23, 24, 25, 26, 27, 28, 29, 30 contiguous nucleotides of SEQ ID NO: 1 and 1, 2, 3, 4, or 5 additional nucleotides in 3' and/or in 5'.

In one embodiment of the invention, the IRS-1 antisense oligonucleotide is GS-101. According to the invention, GS-101 is an antisense oligonucleotide having the sequence

SEQ ID NO: 2
(5'-TCTCCGGAGGGCTCGCCATGCTGCT-3').

In one embodiment, the IRS-1 antisense oligonucleotide is a function conservative sequence of SEQ ID NO: 2, wherein said function conservative sequence comprises from 9 to 50, 12 to 45, 15 to 40, 20 to 35, or 25 to 30 nucleotides that has at least about 75%, 80%, 85%, 90%, 95% or more than about 95%, 96%, 97%, 98%, 99% of identity with SEQ ID NO: 2 and that conserves the capacity of inhibiting IRS-1 expression as SEQ ID NO: 2.

In one embodiment, the function conservative sequence of SEQ ID NO: 2 comprises 9, 10, 11, 12, 13, 14, 15, 16, 17, 18, 19, 20, 21, 22, 23, 24, 25, 26, 27, 28, 29 or 30 nucleotides.

The term "identity" or "identical", when used in a relationship between two or more nucleotide sequences, refers to the degree of sequence relatedness between nucleotide sequences, as determined by the number of matches between strings of two or more bases. "Identity" measures the percent of identical matches between the smaller of two or more sequences with gap alignments (if any) addressed by a particular mathematical model or computer program (i.e., "algorithms"). Identity of related nucleotide sequences can be readily calculated by known methods. Such methods include, but are not limited to, those described in Arthur M. Lesk, *Computational Molecular Biology: Sources and Methods for Sequence Analysis* (New-York: Oxford University Press, 1988); Douglas W. Smith, *Biocomputing: Informatics and Genome Projects* (New-York: Academic Press, 1993); Hugh G. Griffin and Annette M. Griffin, *Computer Analysis of Sequence Data, Part* 1 (New Jersey: Humana Press, 1994); Gunnar von Heinje, *Sequence Analysis in*

*Molecular Biology: Treasure Trove or Trivial Pursuit* (Academic Press, 1987); Michael Gribskov and John Devereux, Sequence Analysis Primer (New York: M. Stockton Press, 1991); and Carillo et al., 1988. *SIAM J. Appl. Math.* 48(5): 1073-1082. Preferred methods for determining identity are designed to give the largest match between the sequences tested. Methods of determining identity are described in publicly available computer programs. Preferred computer program methods for determining identity between two sequences include the GCG program package, including GAP (Devereux et al., 1984. *Nucl. Acid. Res.* 12(1 Pt 1):387-395; Genetics Computer Group, University of Wisconsin Biotechnology Center, Madison, Wis.), BLASTP, BLASTN, TBLASTN and FASTA (Altschul et al., 1990. *J. Mol. Biol.* 215(3):403-410). The BLASTX program is publicly available from the National Center for Biotechnology Information (NCBI) and other sources (BLAST Manual, Altschul et al. NCB/NLM/NIH Bethesda, Md. 20894; Altschul et al., 1990. *J. Mol. Biol.* 215(3):403-410). The well-known Smith Waterman algorithm may also be used to determine identity.

An example of a function conservative sequence of SEQ ID NO: 2 is SEQ ID NO: 3 (5'-TATCCGGAGGGCTCGC-CATGCTGCT-3').

Other examples of function conservative sequences of SEQ ID NO: 2 include, but are not limited to, the following sequences:

```
                                         (SEQ ID NO: 4)
5'-TCTCCGGAGGGCTCGCCATGCTGC-3';

(SEQ ID NO: 5)
5'-TCTCCGGAGGGCTCGCCATGCTG-3';

(SEQ ID NO: 6)
5'-TCTCCGGAGGGCTCGCCATGCT-3';

(SEQ ID NO: 7)
5'-TCTCCGGAGGGCTCGCCATGC-3';

(SEQ ID NO: 8)
5'-TCTCCGGAGGGCTCGCCATG-3';

(SEQ ID NO: 9)
5'-TCTCCGGAGGGCTCGCCAT-3';

(SEQ ID NO: 10)
5'-CTCCGGAGGGCTCGCCATGCTGCT-3';

(SEQ ID NO: 11)
5'-TCCGGAGGGCTCGCCATGCTGCT-3';

(SEQ ID NO: 12)
5'-CCGGAGGGCTCGCCATGCTGCT-3';

(SEQ ID NO: 13)
5'-CGGAGGGCTCGCCATGCTGCT-3';

(SEQ ID NO: 14)
5'-GGAGGGCTCGCCATGCTGCT-3';

(SEQ ID NO: 15)
5'-GAGGGCTCGCCATGCTGCT-3';

(SEQ ID NO: 16)
5'-AGGGCTCGCCATGCTGCT-3';

(SEQ ID NO: 17)
5'-GGCTCGCCATGCTGCT-3';

(SEQ ID NO: 18)
5'-GCTCGCCATGCTGCT-3';

(SEQ ID NO: 19)
5'-CTCGCCATGCTGCT-3';

(SEQ ID NO: 20)
5'-TCGCCATGCTGCT-3';

(SEQ ID NO: 21)
5'-CGCCATGCTGCT-3';

(SEQ ID NO: 22)
5'-TATCCGGAGGGCTCGCCATGCTGC-3';

(SEQ ID NO: 23)
5'-TATCCGGAGGGCTCGCCATGCTG-3';

(SEQ ID NO: 24)
5'-TATCCGGAGGGCTCGCCATGCT-3';

(SEQ ID NO: 25)
5'-TATCCGGAGGGCTCGCCATGC-3';

(SEQ ID NO: 26)
5'-TATCCGGAGGGCTCGCCATG-3';

(SEQ ID NO: 27)
5'-TATCCGGAGGGCTCGCCAT-3';

(SEQ ID NO: 28)
5'-ATCCGGAGGGCTCGCCATGCTGCT-3'.
```

In one embodiment of the invention, said function conservative sequence of SEQ ID NO: 2 of 25, 30, 35, 40, 45 or 50 nucleotides may be a sequence comprising SEQ ID NO: 2 or SEQ ID NO: 3 between other nucleic acids in C-terminal and N-terminal. Said function conservative sequence may also be a 9 to 12 contiguous nucleotides fragment of SEQ ID NO: 2 or SEQ ID NO: 3.

In one embodiment of the invention, said function conservative sequence of SEQ ID NO: 2 is a nucleic acid sequence comprising SEQ ID NO: 21. In one embodiment, said function conservative sequence of SEQ ID NO: 2 is a nucleic acid sequence of 12, 13, 14, 15, 16, 17, 18, 19, 20, 21, 22, 23, 24, 25, 30, 35, 40, 45 or 50 nucleotides comprising SEQ ID NO: 21.

The phosphorothioate oligonucleotide of the invention, such as, for example, the inhibitors of IRS-1 as hereinabove described, may be synthesized by all methods well known by the person skilled in the art, such as chemical synthesis.

In one embodiment, the phosphorothioate oligonucleotide is not conjugated. Preferably, the phosphorothioate oligonucleotide is not conjugated to a lipid (such as for example, to a fatty acid), to a carbohydrate, to another nucleic acid, to a peptide. In one embodiment, the phosphorothioate oligonucleotide is not part of a nanomaterial such for example, to a layered inorganic hydroxide nanohybrid.

In one embodiment, the phosphorothioate oligonucleotide, e.g., the antisense oligonucleotide as described hereinabove is not conjugated to at least one fatty acid.

In one embodiment, the phosphorothioate oligonucleotide of the invention may be sterilized, such as, for example, by filtration, preferably using a filter with a size ranging from about 0.2 to about 0.8 µm, preferably from about 0.4 to about 0.5 µm, and more preferably through a 0.45 µm filter.

In one embodiment, the composition of the invention comprises an amount of at least one phosphorothioate oligonucleotide ranging from about 0.01% to about 3% in weight to the total weight of the composition, preferably from about 0.04% to about 2% w/w and more preferably is of about 1.72% w/w.

In one embodiment, the composition of the invention comprises an amount of at least one phosphorothioate oligonucleotide ranging from about 0.01% to about 3% in weight to the total weight of the composition, preferably from about 0.04% to about 2% w/w and more preferably is of about 0.086% w/w.

In another embodiment, the composition of the invention is an emulsion and comprises an amount of at least one phosphorothioate oligonucleotide ranging from about 0.01% to about 3% in weight to the total weight of the aqueous phase of the emulsion, preferably from about 0.04% to about 2.5% w/w and more preferably is of about 2.11% w/w.

In one embodiment, the composition of the invention comprises from about 0.40 mg/mL to about 1.75, preferably from about 0.50 mg/mL to about 1.75 mg/mL, more preferably from about 0.60 mg/mL to about 1.5 mg/mL of a phosphorothioate oligonucleotide, preferably of an IRS-1 antisense as hereinabove described.

In another embodiment, the composition of the invention comprises from about 0.70 mg/mL to about 1.25 mg/mL of a phosphorothioate oligonucleotide, preferably of an IRS-1 antisense as hereinabove described.

In another embodiment, the composition of the invention comprises from about 0.80 mg/mL to about 1 mg/mL, preferably from about 0.80 mg/mL to about 0.90 mg/mL of a phosphorothioate oligonucleotide, preferably of an IRS-1 antisense as hereinabove described.

In one embodiment, the composition of the invention comprises from about 0.40 mg/mL to about 0.50 mg/mL, preferably about 0.43 mg/mL of a phosphorothioate oligonucleotide, preferably of an IRS-1 antisense as hereinabove described.

In another embodiment, the composition of the invention comprises from about 0.80 mg/mL to about 0.90 mg/mL, preferably about 0.86 mg/mL of a phosphorothioate oligonucleotide, preferably of an IRS-1 antisense as hereinabove described.

In another embodiment, the composition of the invention comprises from about 1.60 mg/mL to about 1.80 mg/mL, preferably about 1.70 mg/mL of a phosphorothioate oligonucleotide, preferably of an IRS-1 antisense as hereinabove described.

In one embodiment of the invention, the composition of the invention comprises at least one fatty acid.

Examples of fatty acids include, but are not limited to:

(1) saturated fatty acids, which have no C=C moieties and include, without limitation, myristic acid, palmitic acid, stearic acid, arachidic acid, behenic acid, lignoceric acid; and (2) unsaturated fatty acids, including, without limitation, the following: monounsaturated fatty acids, which have one C=C group such as palmitoleic acid, oleic acid, and nervonic acid; diunsaturated fatty acids, which have two C=C groups, such as linoleic acid; triunsaturated fatty acids, which have three C=C groups, such as [alpha]-linolenic acid and [gamma]-linolenic acid; tetraunsaturated fatty acids, which have four C=C groups, such as arachidonic acid; and pentaunsaturated fatty acids, which have five C=C groups, such as eicosapentaenoic acid.

Other examples of fatty acids that may be used include, but are not limited to, lauric acid; 14 carbon fatty acids such as myristic acid; 16 carbon fatty acids such as palmitic and palmitoleic acid; 18 carbon fatty acids such as stearic acid, oleic acid, linoleic acid, [alpha]-linolenic acid, and [gamma]-linolenic acid; 20 carbon fatty acids such as eicosapentaenoic acid; 22 carbon fatty acids such as arachidic acid; and 24 carbon fatty acids such as lignoceric acid and nervonic acid.

In one embodiment, the composition of the invention is an emulsion, and the at least one fatty acid is comprised in the oil phase of the emulsion.

In one embodiment, the composition of the invention comprises at least one oil which may be a vegetable oil, for example, castor oil, olive oil, soy oil, sesame oil, cotton seed oil, sweet almond oil or arachis oil; triglycerides, such as, for example, semi-synthetic oils (medium chains triglycerides (MCT) or long chain triglycerides (LCT)); monoglycerides; diglycerides; oily fatty acids; isopropyl myristate; oily fatty alcohols; esters of sorbitol and fatty acids, oily sucrose esters, or a mineral oil, for example, liquid paraffin or petrolatum; and in general any oily substance which is physiologically tolerated and mixtures thereof.

In one embodiment, the composition of the invention is an emulsion, and the oil phase of the emulsion comprises MCT, i.e., a triglyceride oil in which the carbohydrate chain has about 8-12 carbon atoms. Example of MCT oil which may be used in emulsions of the present invention is Miglyol 812 ™ (supplied for example by Dynamit Novel, Sweden). Miglyol 812 ™ is a mixture of triglycerides of the fractionated plant fatty acids C8 and C10, comprising about 2% w/w or less of caproic acid (C6:0), from about 50% w/w and about 65% w/w of caprylic acid (C8:0), from about 30% w/w and about 45% w/w of capric acid (C10:0), about 2% w/w or less of lauric acid (C12:0) and about 1% w/w or less of myristic acid.

In one embodiment of the invention, the amount of the oil in the composition, preferably in the emulsion, ranges from about 1 to about 20% in weight to the total weight of the composition, preferably from about 5% to about 10% w/w, more preferably is of about 8% w/w.

In one embodiment of the invention, the amount of the oil in the emulsion ranges from about 25 to about 75% in weight to the total weight of the oil phase of the emulsion, preferably from about 35% to about 50% w/w, more preferably is of about 43.2% w/w.

In one embodiment of the invention, the composition of the invention comprises at least one emulsifying agent.

Preferably, when the composition of the invention comprises at least one emulsifying agent, the composition is an emulsion. As used herein, the term "emulsifying agent" may be used interchangeably with surfactant.

In one embodiment, the emulsifying agent is in the aqueous and/or in the oil phase.

A surfactant may be used for assisting in dissolving an excipient or an active agent, dispersing a solid or liquid in a composition, enhancing wetting, modifying drop size, or a number of other purposes.

Examples of useful surfactants include, but are not limited to surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated aryl phenols; ethoxylated fatty acids; ethoxylated; fatty esters or oils (animal and vegetal); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives.

In one embodiment, the surfactant is an ethoxylate surfactant. An ethoxylate surfactants is one that comprises the moiety —O(CH$_2$CH2O)$_n$—OH, wherein n is at least about 1.

In one embodiment, n ranges from about 1 to about 10,000, preferably from 1 to about 1000, more preferably from about 1 to about 500.

Some ethoxylates contain one ethoxylate moiety. In other words, there is a single ethoxylate chain on each molecule. Examples of surfactants with one ethoxylate moiety, include, but are not limited to, ethoxylated alcohols wherein the alcohol has a single hydroxyl unit; alkylphenol ethoxylates; ethoxylated fatty acids; fatty acid methyl ester ethoxylates; polyethylene glycols; and the like.

Examples of ethoxylated alcohols include, but are not limited to:

Ethoxylates of linear alcohols having from about 6 to about 20 carbon atoms, preferably from about 10 to about 16 carbon atoms. In another embodiment, n ranges from about 1 to about 100, preferably from about 1 to about 50, such as, for example, from about 5 to about 50 ethylene oxide units, or from about 1 to about 20 ethylene oxide units, or from about 30 to about 50 ethylene oxide units;

Ethoxylated alkylphenols which are alkylphenols that are ethoxylated, i.e., the phenolic OH is replaced with an ethoxylate moiety. These include but are not limited to: octylphenol ethoxylate, i.e., C$_8$H$_{17}$Ph(OCH$_2$CH2O)$_n$H; nonylphenol ethoxylate, i.e., C$_9$H$_{19}$Ph(OCH$_2$CH2O)$_n$H; alkylphenols of the above formula wherein n is from about 1 to about 100;

Ethoxylated fatty acids, which include but are not limited to: ethoxylates which are esterified to form either: monoesters, i.e., RCO$_2$ (CH$_2$CH$_2$O)$_n$OH, where RCO$_2$H is a fatty acid; or diesters, i.e., RCO$_2$ (CH$_2$CH$_2$O)$_n$C(=O)R.

Ethoxylates may comprise more than one ethoxylate moiety. In other words, there may be ethoxylate moieties attached to several different parts of the molecule. Examples include, but are not limited to, block polymers; ethoxylated oils; sorbitan derivatives; sucrose and glucose ethoxylates; and the like.

Block polymers are polymers with the structure A-B-A', wherein A and A' are polyethylene chains of 1 or more ethylene units, and B is a polypropylene chain of one or more propylene units. Generally, but not necessarily, A and A' are approximately the same length.

In one embodiment, A and A' contain from about 2 to about 200 ethylene units, preferably from about 5 to about 100 ethylene units, preferably from about 7 to about 15 ethylene units, more preferably about 7, about 8, or about 12 ethylene units. In another embodiment, B contains from about 25 to about 100 propylene units, preferably from about 30 to about 55 propylene units, more preferably about 30, about 34, or about 54 propylene units. In another embodiment, the molecular weight of the block polymers is from about 1000 g/mol to about 20000 g/mol, preferably from about 2000 g/mol to about 10000 g/mol, preferably about 2500 g/mol, about 3000 g/mol, about 3800 g/mol, or about 8400 g/mol.

Examples of block polymers include, but are not limited to:

Poloxalene: wherein A has about 12 ethylene oxide units, B has about 34 propylene oxide units, A' has about 12 ethylene oxide units, and the average molecular weight is about 3000 g/mol;

Poloxamer 182: wherein A has about 8 ethylene oxide units, B has about 30 propylene oxide units, A' has about 8 ethylene oxide units, and the average molecular weight is about 2500 g/mol;

Poloxamer 188: wherein A has about 75 ethylene oxide units, B has about 30 propylene oxide units, A' has about 75 ethylene oxide units, and the average molecular weight is about 8400 g/mol;

Poloxamer 331: wherein A has about 7 ethylene oxide units, B has about 54 propylene oxide units, A' has about 7 ethylene oxide units, and the average molecular weight is about 3800 g/mol.

Ethoxylated fatty esters or oils (animal and vegetal) are products which result from reacting ethylene oxide with a fatty ester or an oil. When a fatty oil is used, the products is a mixture of ethoxylates of the fatty acids present in the oil, ethoxylates of glycerin, ethoxylates of mono and diglycerides, and the like. Specific examples include, but are not limited to: ethoxylates of the following oils: anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil and sesame oil, coriander oil, lavender oil, citronella oil, juniper oil, lemon oil, orange oil, clary sage oil, nutmeg oil, tea tree oil, coconut oil, tallow oil, and lard. In one embodiment, from 1 to about 50 moles of ethylene oxide is used per mole of the oil triglyceride. In another embodiment, from about 30 to about 40 moles of ethylene oxide is used per mole of the oil triglyceride.

Ethylene oxide may also react with a fatty acid ester with a formula RCO$_2$R' to form RCO$_2$(CH$_2$CH$_2$O)$_n$R. Thus, surfactants having the formula RCO$_2$(CH$_2$CH$_2$O)$_n$R', where RCO$_2$H is a fatty acid and R' is alkyl having from 1 to 6 carbons are contemplated.

In one embodiment, the surfactant is a fatty acid methyl ester ethoxylate, wherein R' is methyl.

Other examples of RCO$_2$H include, but are not limited to, lauric acid; a 14-carbon fatty acid such as myristic acid; a 16-carbon fatty acid such as palmitic and palmitoleic acid; 18-carbon fatty acids such as stearic acid, oleic acid, linoleic acid, [alpha]-linolenic acid, and [gamma]-linolenic acid; a 20-carbon fatty acids such as eicosapentaenoic acid; a 22-carbon fatty acids such as arachidic acid; or a 24-carbon fatty acids such as lignoceric acid and nervonic acid.

In one embodiment, the surfactant is a polyethylene glycol. Polyethylene glycols are ethoxylates that are unsubstituted, or terminated with oxygen on both ends, i.e., HO(CH$_2$CH$_2$O)$_n$H.

In one embodiment, the surfactant is a sorbitan derivative. Sorbitan derivatives are ethoxylated sorbates having a fatty acid capping one or more of the ethoxylated chains.

These include, but are not limited to: (A) sorbitan derivatives wherein the total number of ethylene oxide units is from 3 to 30; (B) sorbitan derivatives wherein the total number of ethylene oxide units is 4, 5, or 20; (C) sorbitan derivatives wherein the capping acid is laurate, palmitate, stearate, or oleate.

The sorbitan derivative may be a polyoxyethylene (POE) sorbitan monolaurate, a POE sorbitan dilaurate, a POE sorbitan trilaurate, a POE sorbitan monopalmitate, a POE sorbitan dipalmitate, a POE sorbitan tripalmitate, a POE sorbitan monostearate, a POE sorbitan distearate, a POE sorbitan tristearate, a POE sorbitan monooleate, a POE sorbitan dioleate, and/or a POE sorbitan trioleate.

Specific examples include but are not limited to: POE (20) sorbitan monolaurate, POE (4) sorbitan monolaurate, POE

(20) sorbitan monopalmitate, POE (20) monostearate, POE (20) sorbitan monostearate, POE (4) sorbitan monostearate, POE (20) sorbitan tristearate, POE (20) sorbitan monoleate, POE (20) sorbitan 15 monoleate, POE (5) sorbitan 10 monoleate, and/or POE (20) sorbitan trioleate.

In one embodiment, the surfactant is a sucrose or glucose ester, or a derivative thereof. Sucrose and glucose esters and derivatives include, but are not limited to, polyvinyl alcohol, povidone, hydroxypropyl methyl cellulose, poloxamers, carboxymethyl cellulose, hydroxyethyl cellulose, and acrylates (e.g., Pemulen(R)).

Other examples of suitable emulsifying agents include, but are not limited to, naturally-occurring gums, for example, gum acacia or gum tragacanth; naturally-occurring phosphatides, for example, soya bean lecithin, and esters or partial esters derived from fatty acids and hexitol anhydrides, for example, sorbitan mono-oleate, and condensation products of the said partial esters with ethylene oxide, for example, polyoxyethylene sorbitan mono-oleate; sorbitan ester such as, for example, sorbitan stearate, sorbitan mono laurate, polyoxyethylene sorbitan mono oleate and sorbitan monopalmitate; bentonite; glycerin monostearate; glyceryl monooleate and propylene glycol monolaurate or mixtures thereof; glyceryl stearate; Poloxamer 188; Poloxamer 282; Poloxamer 407; tyloxapol; vitamin E D-polyethylene glycol succinate; polyethylene glycol (PEG)(such as, for example, PEG 75); cetostearyl alcohol; cholesterol; ethylene glycol palmitostearate; lauric acid; myristic acid; myristyl alcohol; linoleic acid; oleic acid; palmitic acid; polysorbate 20 (Tween 20), sorbitan trioleate (Span 85), phospholipids such as egg lecithin stearic acid oleyl alcohol; and mixture thereof.

In one embodiment, the composition of the invention is an emulsion, and the emulsifying agent is comprised in the oil phase. In one embodiment, the emulsion of the invention comprises glyceryl stearate and PEG75 as emulsifying agent. A mixture of glyceryl stearate and PEG75 is commercially available as Gelot 64®.

In one embodiment, the amount of emulsifying agent in the emulsion ranges from about 1% to about 10% in weight to the total weight of the emulsion, preferably from about 2.5% to about 5% w/w, more preferably is of about 3.5% w/w.

In one embodiment, the amount of emulsifying agent in the emulsion ranges from about 5% to about 40% in weight to the total weight of the oil phase of the emulsion, preferably from about 10% to about 30% w/w, more preferably is of about 18.9% w/w.

In one embodiment, the composition of the invention further comprises a thickening agent.

Examples of suitable thickening agents include, but are not limited to, beeswax, hard paraffin and cetyl alcohol. Advantageously, said thickening agent is cetyl alcohol.

In one embodiment, the composition of the invention is an emulsion, and the thickening agent is comprised in the oil phase of the emulsion.

In one embodiment, the amount of thickening agent in the composition, preferably in the emulsion, ranges from about 0.1% to about 10% in weight to the total weight of the composition, preferably from about 0.5% to about 5% w/w, more preferably is of about 2% w/w.

In one embodiment, the amount of thickening agent in the emulsion ranges from about 1% to about 30% in weight to the total weight of the oil phase of the emulsion, preferably from about 5% to about 20% w/w, more preferably is of about 10.8% w/w.

In one embodiment, the composition of the invention further comprises an osmolality modifying agent.

Examples of suitable osmolality modifying agents include, but are not limited to, NaCl, KCl, $CaCl_2$, glycerol, mannitol, alpha-trehalose and propylene-glycol.

In one embodiment, the composition of the invention is an emulsion, and the osmolality modifying agent is advantageously comprised in the oil phase of the emulsion. An example of suitable osmolality modifying agent present in the oil phase of the emulsion is glycerol.

In one embodiment of the invention, the amount of osmolality modifying agent in the composition, preferably in the emulsion, ranges from about 0.5% to about 25% in weight to the total weight of the composition, preferably from about 1% to about 10% w/w, more preferably is of about 5% w/w.

In one embodiment of the invention, the amount of osmolality modifying agent in the emulsion ranges from about 10% to about 45% in weight to the total weight of the oil phase of the emulsion, preferably from about 20% to about 35% w/w, more preferably is of about 27% w/w.

The composition of the invention further comprises at least one agent comprising a thiol group.

In one embodiment, the at least one agent comprising a thiol group is not the phosphorothioate oligonucleotide.

Examples of agents comprising a thiol group include, but are not limited to, lipoic acid, DL-cysteine, N-acetylcysteine, creatinine, glutathione, 2-mercapto-5-benzimidazole salts, 2-mercaptoethanesulfonic acid salts, Na-edetate, Na-bisulfite and Na-sulfite. Preferably, the at least one agent comprising a thiol group is selected from the group comprising DL-cysteine, N-acetylcysteine and lipoic acid.

In one embodiment, the agent comprising a thiol group is selected from lipoic acid, DL-cysteine, N-acetylcysteine, creatinine, glutathione, 2-mercapto-5-benzimidazole salts, 2-mercaptoethanesulfonic acid salts. Preferably, the at least one agent comprising a thiol group is selected from the group comprising DL-cysteine, N-acetylcysteine and lipoic acid.

Preferably, the composition of the invention is an emulsion, and the at least one agent comprising a thiol group is comprised in the aqueous phase of the emulsion.

In one embodiment, the amount of the at least one agent comprising a thiol group in the composition, preferably in the emulsion, ranges from about 0.5% to about 5% in weight to the total weight of the composition, preferably from about 1 to about 3% w/w, more preferably is of about 2% w/w.

In one embodiment, the amount of the at least one agent comprising a thiol group in the composition, preferably in the emulsion, ranges from about 0.01% to about 2% in weight to the total weight of the composition, preferably from about 0.05% to about 0.5% w/w, more preferably is of about 0.1% w/w.

In one embodiment, the amount of the at least one agent comprising a thiol group in the composition, preferably in the emulsion, ranges from about 0.05% to about 2% in weight to the total weight of the composition, preferably from about 0.1% to about 1% w/w, more preferably is of about 0.25% w/w.

In one embodiment, the amount of the at least one agent comprising a thiol group in the emulsion of the invention ranges from about 0.5% to about 5% in weight to the total weight of the aqueous phase, preferably from about 1 to about 3% w/w, more preferably is of about 2.45% w/w.

The composition of the invention further comprises at least one phosphate compound.

In one embodiment, the phosphate compound is not the phosphorothioate oligonucleotide.

Examples of phosphate compounds include, but are not limited to, $Na_2HPO_4$ (sodium hydrogen phosphate), $NaH_2PO_4$ (sodium dihydrogen phosphate), $Na_3PO_4$ (sodium phosphate), $K_2HPO_4$ (potassium hydrogen phosphate), $K_3PO_4$ (potassium phosphate), $KH_2PO_4$ (monopotassium phosphate), $(NH_4)_2HPO_4$ (ammonium hydrogen phosphate), $(NH_4)_3PO_4$ (ammonium phosphate), $Mg(H_2PO_4)_2$ (magnesium dihydrogen phosphate), $Mg_3(PO_4)_2$ (magnesium phosphate), $MgHPO_4$ (magnesium hydrogen phosphate), $MgNH_4PO_4$ (magnesium ammonium phosphate), $Ca(H_2PO_4)_2$ (calcium dihydrogen phosphate), $CaHPO_4$ (dicalcium phosphate), $Ca_3(PO_4)_2$ (tricalcium phosphate), $Ca_8(HPO_4)_2(PO_4)_4$ (octacalcium phosphate), $H_2PO_4$ (dihydrogen phosphate), $H_3PO_4$ (phosphoric acid), $Ba_3(PO_4)_2$ (barium phosphate), $Co_3(PO_4)_2$ (cobalt(II) phosphate), $CoPO_4$ (cobalt(III) phosphate), $Cr_3(PO_4)_2$ (chromium(II) phosphate), $Cu_3(PO_4)_2$ (copper(II) phosphate), $Fe_3(PO_4)_2$ (iron(II) phosphate), $FePO_4$ (iron(III) phosphate), $Li_3PO_4$ (lithium phosphate), $Ni_3(PO_4)_2$ (nickel(II) phosphate), $Pb_3(PO_4)_2$ (lead(II) phosphate), $Pb_3(SO_4)_4$ (lead(IV) phosphate), $Sn_3(PO_4)_2$ (tin(II) phosphate), $Sr_3(PO_4)_2$ (strontium phosphate), $V_3(PO_4)_5$ (vanadium(V) phosphate), and $Zn_3(PO_4)_2$ (zinc(II) phosphate. Preferably, the at least one phosphate compound is selected from the group comprising $Na_2HPO_4$, $NaH_2PO_4$, $Na_3PO_4$, $K_2HPO_4$, $K_3PO_4$, $KH_2PO_4$, $(NH_4)_2HPO_4$, $(NH_4)_3PO_4$, $Mg(H_2PO_4)_2$, $Mg_3(PO_4)_2$, $MgHPO_4$, $MgNH_4PO_4$, $Ca(H_2PO_4)_2$, $CaHPO_4$, $Ca_3(PO_4)_2$, $Ca_8(HPO_4)_2(PO_4)_4$, $H_2PO_4$ and $H_3PO_4$. More preferably, the at least one phosphate compound is selected from the group comprising $Na_2HPO_4$, $NaH_2PO_4$, $K_2HPO_4$ and $KH_2PO_4$.

In one embodiment, the phosphate compound is selected from $Na_2HPO_4$, $NaH_2PO_4$, $Na_3PO_4$, $K_2HPO_4$, $K_3PO_4$, and $KH_2PO_4$. Preferably, the at least one phosphate compound is selected from the group comprising $Na_2HPO_4$, $NaH_2PO_4$, and $Na_3PO_4$.

Preferably, the composition of the invention is an emulsion, and the at least one phosphate compound is comprised in the aqueous phase of the emulsion.

In one embodiment, the amount of the at least one phosphate compound in the composition, preferably in the emulsion, ranges from about 0.05% to about 2% in weight to the total weight of the composition, preferably from about 0.1% to about 1% w/w, more preferably from about 0.3% to about 0.7% w/w, even more preferably is of about 0.4-0.6% w/w.

In one embodiment, the amount of the at least one phosphate compound in the emulsion of the invention ranges from about 0.01% to about 2% in weight to the total weight of the aqueous phase, preferably from about 0.1% to about 1% w/w, more preferably is of about 0.5% w/w.

In one embodiment, the amount of the at least one phosphate compound in the composition of the invention ranges from about 0.1 mM to about 100 mM final of the total composition, preferably from about 1 mM to about 50 mM, more preferably is of about 15 mM.

In one embodiment, the at least one phosphate compound is present as a phosphate acid/base conjugate pair. Examples of phosphate acid/base conjugate pairs include, but are not limited to, $NaH_2PO_4/Na_2HPO_4$, $KH_2PO_4/K_2HPO_4$, $Na_2HPO_4/Na_3PO_4$, and $K_2HPO_4/K_3PO_4$, wherein the first member of the pair is the acid and the second member of the pair is the conjugated base.

In one embodiment, the ratio of the phosphate acid to phosphate base in the acid/base conjugate pairs ranges between about 1:2 to about 1:20, preferably from about 1:2 to about 1:12.

In one embodiment, the amount of phosphate acid ranges from about 5% to about 30% in weight to the total weight of the phosphate acid/base conjugate pairs, preferably from about 7.5% w/w to about 25% w/w. In one embodiment, the amount of phosphate base ranges from about 70% to about 95% in weight to the total weight of the phosphate acid/base conjugate pairs, preferably from about 75% w/w to about 92.5% w/w.

In one embodiment, the composition of the invention may further comprise another emulsifying agent such as a viscosity modifying agent.

In one embodiment, the composition comprises 15 mM of at least one phosphate compound, preferably selected from $Na_2HPO_4$, $NaH_2PO_4$, $Na_3PO_4$, $K_2HPO_4$, $K_3PO_4$, $KH_2PO_4$ and mixtures thereof, and 0.25% N-acetylcysteine.

Examples of viscosity modifying agents include, but are not limited to, a hydrogel of sodium hyaluronate, polymers of acrylic acid, for example polymers of acrylic acids cross-linked with polyalkenyl ethers or divinyl glycol, such as, for example, Carbopol® gels (also known as carbomers), hydroxyethyl cellulose, dextran, carboxymethyl cellulose, polyethylene glycol, polyvinyl alcohol and collagen.

In one embodiment, the composition of the invention is an emulsion, and the viscosity modifying agent is comprised in the aqueous phase. In an embodiment of the invention, the viscosity modifying agent is a Carbopol®, such as, for example, Carbopol® 980 NF. A Carbopol® is a homopolymer of acrylic acid, cross-linked with an allyl ether of pentaerythritol, an allyl ether of sucrose, or an allyl ether of propylene. In said embodiment, the viscosity modifying agent is in the aqueous phase of the emulsion.

In one embodiment of the invention, the amount of the viscosity modifying agent in the composition, preferably in the emulsion, ranges from about 0.01% to about 0.1% in weight to the total weight of the composition, preferably from about 0.03% to about 0.08% w/w, more preferably is of about 0.05% w/w.

In one embodiment of the invention, the amount of the viscosity modifying agent in the composition, preferably in the emulsion, ranges from about 0.01% to about 0.3% in weight to the total weight of the composition, preferably from about 0.05% to about 0.2% w/w, more preferably is of about 0.1% w/w.

In one embodiment of the invention, the amount of the viscosity modifying agent in the emulsion ranges from about 0.01% to about 0.2% in weight to the total weight of the aqueous phase of the emulsion, preferably from about 0.03% to about 0.1% w/w, more preferably is of about 0.061% w/w.

In one embodiment of the invention, the amount of the viscosity modifying agent in the emulsion ranges from about 0.01% to about 0.3% in weight to the total weight of the aqueous phase of the emulsion, preferably from about 0.07% to about 0.2% w/w, more preferably is of about 0.123% w/w.

In one embodiment, the composition of the invention further comprises a pH buffering agent.

Indeed, preferably, the pH of the composition of the emulsion is constant, and ranges from about 6 to about 8, preferably from about 6.8 to about 7.2, more preferably is of about 7.

Suitable examples of pH buffering agents include, but are not limited to, NaOH, phosphate buffer, citrate buffer, tris buffer, histidine buffer and acetate buffer. In one embodiment, the pH buffering agent is NaOH.

In one embodiment, the composition of the invention is an emulsion, and the pH buffering agent is advantageously present in the aqueous phase of the emulsion.

In one embodiment of the invention, the amount of pH buffering agent in the composition, preferably in the emulsion, is sufficient for buffering the composition at the desired pH.

In one embodiment, the amount of pH buffering agent in the composition, preferably in the emulsion, ranges from about 0.1% to about 0.5% in weight to the total weight of the composition, preferably of the emulsion, preferably from about 0.2% to about 0.4% w/w, more preferably is of about 0.29% w/w.

In one embodiment of the invention, the composition is an emulsion, and the amount of pH buffering agent in the emulsion ranges from about 0.2% to about 0.5% in weight to the total weight of the aqueous phase of the emulsion, preferably from about 0.3% to about 0.4% w/w, more preferably is of about 0.35% w/w.

In one embodiment of the invention, the composition of the invention further comprises urea. Urea may help to denature secondary structures in the active phosphorothioate oligonucleotide present in the composition of the invention.

In one embodiment, the composition of the invention is an emulsion, and urea is preferably comprised in the aqueous phase of the emulsion.

In one embodiment, the amount of urea in the composition, preferably in the emulsion, ranges from about 0.5% to about 20% in weight to the total weight of the composition, preferably from about 1% to about 10% w/w, more preferably is of about 4% w/w.

In one embodiment, the amount of urea in the emulsion of the invention ranges from about 0.5% to about 20% in weight to the total weight of the aqueous phase of the emulsion of the invention, preferably from about 1% to about 10% w/w, more preferably is of about 4.9% w/w.

In one embodiment, the composition of the invention is an oil-in-water emulsion or a water-in-oil-in-water emulsion, preferably a water-in-oil-in-water emulsion, wherein said emulsion comprises:
- an aqueous phase, wherein the amount of the aqueous phase in the emulsion ranges from about 70 to 99% in weight to the total weight of the emulsion, preferably is of about 81.5% w/w; and
- an oil phase, wherein the amount of the oil phase in the emulsion ranges from about 1 to about 30% in weight to the total weight of the emulsion, preferably is of about 18.5% w/w.

In one embodiment, the composition of the invention is an oil-in-water emulsion or a water-in-oil-in-water emulsion, preferably a water-in-oil-in-water emulsion, wherein said emulsion comprises:
- an aqueous phase, wherein the amount of the aqueous phase in the emulsion ranges from about 70 to 99% in weight to the total weight of the emulsion, preferably is of about 86.5% w/w; and
- an oil phase, wherein the amount of the oil phase in the emulsion ranges from about 1 to about 30% in weight to the total weight of the emulsion, preferably is of about 13.5% w/w.

In one embodiment, the aqueous phase in the emulsion comprises:
  a phosphorothioate oligonucleotide;
  at least one agent comprising a group thiol;
  at least one phosphate compound;
  optionally, a viscosity modifying agent;
  optionally, a pH buffering agent; and
  optionally, urea.

In one embodiment, the aqueous phase in the emulsion comprises:
  a phosphorothioate oligonucleotide;
  at least one agent comprising a group thiol;
  at least one phosphate compound;
  optionally, a viscosity modifying agent; and
  optionally, urea.

31

In one embodiment, the oil phase in the emulsion comprises:
  an oil;
  optionally, at least one emulsifying agent;
  optionally a thickening agent; and
  optionally, an osmolality modifying agent.

In one embodiment, the composition of the invention is an oil-in-water emulsion or a water-in-oil-in-water emulsion, preferably a water-in-oil-in-water emulsion, wherein said emulsion comprises:
  an aqueous phase, wherein the amount of the aqueous phase in the emulsion ranges from about 70 to 99% in weight to the total weight of the emulsion, preferably is of about 81.5% w/w; and
  an oil phase, wherein the amount of the oil phase in the emulsion ranges from about 1 to about 30% in weight to the total weight of the emulsion, preferably is of about 18.5% w/w;
  wherein
  the aqueous phase comprises:
    a phosphorothioate oligonucleotide;
    at least one agent comprising a group thiol;
    at least one phosphate compound;
    optionally, a viscosity modifying agent;
    optionally, a pH buffering agent;
    optionally, urea; and
  the oil phase comprises:
    an oil;
    optionally, at least one emulsifying agent;
    optionally a thickening agent; and
    optionally, an osmolality modifying agent.

In one embodiment, the composition of the invention is an oil-in-water emulsion or a water-in-oil-in-water emulsion, preferably a water-in-oil-in-water emulsion, wherein said emulsion comprises:
  an aqueous phase, wherein the amount of the aqueous phase in the emulsion ranges from about 70 to 99% in weight to the total weight of the emulsion, preferably is of about 86.5% w/w; and
  an oil phase, wherein the amount of the oil phase in the emulsion ranges from about 1 to about 30% in weight to the total weight of the emulsion, preferably is of about 13.5% w/w;
  wherein
  the aqueous phase comprises:
    a phosphorothioate oligonucleotide;
    at least one agent comprising a group thiol;
    at least one phosphate compound;
    optionally, a viscosity modifying agent;
    optionally, a pH buffering agent;
    optionally, urea; and
  the oil phase comprises:
    an oil;
    optionally, at least one emulsifying agent;
    optionally a thickening agent; and
    optionally, an osmolality modifying agent.

In one embodiment, the composition of the invention is an oil-in-water emulsion or a water-in-oil-in-water emulsion, preferably a water-in-oil-in-water emulsion, wherein said emulsion comprises:
- an aqueous phase, wherein the amount of the aqueous phase in the emulsion ranges from about 70 to 99% in weight to the total weight of the emulsion, preferably is of about 81.5% w/w or 86.5% w/w; and
- an oil phase, wherein the amount of the oil phase in the emulsion ranges from about 1 to about 30% in weight to the total weight of the emulsion, preferably is of about 18.5% w/w or 13.5% w/w;
wherein
the aqueous phase comprises:
- a phosphorothioate oligonucleotide;
- at least one agent comprising a group thiol;
- at least one phosphate compound;
- optionally, a viscosity modifying agent;
- optionally, urea; and the oil phase comprises:
- an oil;
- optionally, at least one emulsifying agent;
- optionally a thickening agent; and
- optionally, an osmolality modifying agent.

In one embodiment, the composition of the invention is an oil-in-water emulsion or a water-in-oil-in-water emulsion, preferably a water-in-oil-in-water emulsion, wherein said emulsion comprises:
- an aqueous phase, wherein the amount of the aqueous phase in the emulsion ranges from about 70 to 99% in weight to the total weight of the emulsion, preferably is of about 81.5% w/w or 86.5% w/w; and
- an oil phase, wherein the amount of the oil phase in the emulsion ranges from about 1 to about 30% in weight to the total weight of the emulsion, preferably is of about 18.5% w/w or 13.5% w/w;
wherein
the aqueous phase comprises:
- a phosphorothioate oligonucleotide;
- at least one agent comprising a group thiol selected from the group consisting of DL-cysteine, N-acetyl-cysteine and lipoic acid;
- at least one phosphate compound selected from the group consisting of $Na_2HPO_4$, $NaH_2PO_4$, $K_2HPO_4$ and $KH_2PO_4$, preferably a $NaH_2PO_4/Na_2HPO_4$ or $KH_2PO_4/K_2HPO_4$ conjugate pair;
- optionally, a viscosity modifying agent selected from the group consisting of hydrogel of sodium hyaluronate, polymers of acrylic acid, hydroxyethyl cellulose, dextran, carboxymethyl cellulose, polyethylene glycol, polyvinyl alcohol and collagen, preferably a Carbopol® gel, more preferably Carbopol® 980 NF;
- optionally, a pH buffering agent selected from the group consisting of NaOH, phosphate buffer, citrate buffer, tris buffer, histidine buffer and acetate buffer, preferably NaOH;
- optionally, urea; and the oil phase comprises:
- an oil selected from the group consisting of vegetable oil, triglycerides, monoglycerides, diglycerides, oily fatty acids, isopropyl myristate, oily fatty alcohols, esters of sorbitol and fatty acids, oily sucrose esters and mineral oils, preferably MCT, more preferably Miglyol 812™;
- optionally, at least one emulsifying agent selected from the group consisting of ethoxylate surfactants, polyethylene glycols (PEGs), sorbitan derivatives, sucrose or glucose esters, naturally-occurring gums, naturally-occurring phosphatides, esters or partial esters derived from fatty acids and hexitol anhydrides, condensation products of the said partial esters with ethylene oxide, bentonite, glycerin monostearate, glyceryl monooleate, propylene glycol monolaurate, glyceryl stearate, Poloxamer, tyloxapol, vitamin E, D-polyethylene glycol succinate, cetostearyl alcohol, cholesterol, ethylene glycol palmitostearate, lauric acid, myristic acid, myristyl alcohol, linoleic acid, oleic acid, palmitic acid, polysorbate 20 (Tween 20), sorbitan trioleate (Span 85), phospholipids, and mixture thereof, preferably a mixture of glyceryl stearate and PEG, preferably a mixture of glyceryl stearate and PEG75, preferably Gelot 64®;
- optionally a thickening agent selected from the group consisting of beeswax, hard paraffin and cetyl alcohol, preferably cetyl alcohol; and
- optionally, an osmolality modifying agent selected from the group consisting of NaCl, KCl, $CaCl_2$, glycerol, mannitol, alpha-trehalose and propylene-glycol, preferably glycerol.

In one embodiment, the composition of the invention is an oil-in-water emulsion or a water-in-oil-in-water emulsion, preferably a water-in-oil-in-water emulsion, wherein said emulsion comprises:
- an aqueous phase, wherein the amount of the aqueous phase in the emulsion ranges from about 70 to 99% in weight to the total weight of the emulsion, preferably is of about 81.5% w/w or 86.5% w/w; and
- an oil phase, wherein the amount of the oil phase in the emulsion ranges from about 1 to about 30% in weight to the total weight of the emulsion, preferably is of about 18.5% w/w or 13.5% w/w;
wherein
the aqueous phase comprises:
- a phosphorothioate oligonucleotide;
- at least one agent comprising a group thiol selected from the group consisting of DL-cysteine, N-acetyl-cysteine and lipoic acid;
- at least one phosphate compound selected from the group consisting of $Na_2HPO_4$, $NaH_2PO_4$, $K_2HPO_4$ and $KH_2PO_4$, preferably a $NaH_2PO_4/Na_2HPO_4$ or $KH_2PO_4/K_2HPO_4$ conjugate pair;
- optionally, a viscosity modifying agent selected from the group consisting of hydrogel of sodium hyaluronate, polymers of acrylic acid, hydroxyethyl cellulose, dextran, carboxymethyl cellulose, polyethylene glycol, polyvinyl alcohol and collagen, preferably a Carbopol® gel, more preferably Carbopol® 980 NF;
- optionally, urea; and the oil phase comprises:
- an oil selected from the group consisting of vegetable oil, triglycerides, monoglycerides, diglycerides, oily fatty acids, isopropyl myristate, oily fatty alcohols, esters of sorbitol and fatty acids, oily sucrose esters and mineral oils, preferably MCT, more preferably Miglyol 812™;
- optionally, at least one emulsifying agent selected from the group consisting of ethoxylate surfactants, polyethylene glycols (PEGs), sorbitan derivatives, sucrose or glucose esters, naturally-occurring gums, naturally-occurring phosphatides, esters or partial esters derived from fatty acids and hexitol anhydrides, condensation products of the said partial esters with ethylene oxide, bentonite, glycerin monostearate, glyceryl monooleate, propylene glycol monolaurate, glyceryl stearate, Poloxamer, tyloxapol, vitamin E, D-polyethylene glycol succinate, cetostearyl alcohol, cholesterol, ethylene glycol palmitostearate, lauric acid, myristic acid, myristyl alcohol, linoleic acid, oleic acid, palmitic acid, polysorbate 20 (Tween 20), sorbitan trioleate (Span 85), phospholipids, and mixture thereof, preferably a mixture of glyceryl stearate and PEG, preferably a mixture of glyceryl stearate and PEG75, preferably Gelot 64®;

optionally a thickening agent selected from the group consisting of beeswax, hard paraffin and cetyl alcohol, preferably cetyl alcohol; and optionally, an osmolality modifying agent selected from the group consisting of NaCl, KCl, $CaCl_2$, glycerol, mannitol, alpha-trehalose and propyleneglycol, preferably glycerol.

In one embodiment, the composition of the invention is an oil-in-water emulsion or a water-in-oil-in-water emulsion, preferably a water-in-oil-in-water emulsion, wherein said emulsion comprises:

an aqueous phase, wherein the amount of the aqueous phase in the emulsion ranges from about 70 to 99% in weight to the total weight of the emulsion, preferably is of about 81.5% w/w or 86.5% w/w; and an oil phase, wherein the amount of the oil phase in the emulsion ranges from about 1 to about 30% in weight to the total weight of the emulsion, preferably is of about 18.5% w/w or 13.5% w/w;

wherein the aqueous phase comprises:

a phosphorothioate oligonucleotide, preferably in an amount ranging from about 0.01% to about 3% in weight to the total weight of the emulsion, preferably from about 0.04% to about 2% w/w and more preferably is of about 1.72% w/w or of about 0.086% w/w; or in an amount ranging from about 0.01% to about 3% in weight to the total weight of the aqueous phase of the emulsion, preferably from about 0.04% to about 2.5% w/w and more preferably is of about 2.11% w/w; and at least one agent comprising a group thiol, preferably in an amount ranging from about 0.5% to about 5% in weight to the total weight of the emulsion, preferably from about 1 to about 3% w/w, more preferably is of about 2% w/w; or in an amount ranging from about 0.5% to about 5% in weight to the total weight of the aqueous phase of the emulsion of the invention, preferably from about 1 to about 3% w/w, more preferably is of about 2.45% w/w; and at least one phosphate compound, preferably in an amount ranging from about 0.05% to about 2% in weight to the total weight of the emulsion, preferably from about 0.1% to about 1% w/w, more preferably from about 0.3% to about 0.7% w/w, even more preferably is of about 0.4-0.6% w/w; or in an amount ranging from about 0.01% to about 2% in weight to the total weight of the aqueous phase of the emulsion of the invention, preferably from about 0.1% to about 1% w/w, more preferably is of about 0.5% w/w; and optionally, a viscosity modifying agent, preferably in an amount ranging from about 0.01 to about 0.1% in weight to the total weight of the emulsion, more preferably of about 0.05% w/w, or ranging from about 0.01% to about 0.2% in weight to the weight of the aqueous phase, preferably of about 0.061% w/w; and optionally, a pH buffering agent, preferably in an amount sufficient for providing a pH ranging from about 6 to about 8, preferably from about 6.8 to about 7.2, more preferably of about 7; such as, for example, in an amount ranging from about 0.1 to about 0.5% in weight to the total weight of the emulsion, preferably of about 0.29% w/w, or ranging from about 0.2% to about 0.5% in weight to the weight of the aqueous phase, preferably of about 0.35% w/w; and optionally, urea, in an amount ranging from about 0.5 to about 20% in weight to the total weight of the emulsion, preferably of about 4% w/w, or ranging from about 0.5% to about 20% in weight to the weight of the aqueous phase, preferably of about 4.9% w/w; and the oil phase comprises:

an oil, preferably in an amount ranging from about 1 to about 20% in weight to the total weight of the emulsion, preferably of about 8% w/w, or ranging from about 25% to about 75% in weight to the total weight of the oil phase, preferably of about 43.2% w/w; and optionally, at least one emulsifying agent, preferably in an amount ranging from about 1 to about 10% in weight to the total weight of the emulsion, preferably of about 3.5% w/w, or ranging from about 5% to about 40% in weight to the total weight of the oil phase, preferably of about 18.9% w/w; and optionally a thickening agent, preferably in an amount ranging from about 0.1 to about 10% in weight to the total weight of the emulsion, preferably of about 2% w/w, or ranging from about 1% to about 30% in weight to the total weight of the oil phase, preferably of about 10.8% w/w; and optionally, an osmolality modifying agent, preferably in an amount ranging from about 0.5 to about 25% in weight to the total weight of the emulsion, preferably of about 5% w/w, or ranging from about 10% to about 45% in weight to the total weight of the oil phase, preferably of about 27% w/w.

In one embodiment, the composition of the invention is an oil-in-water emulsion or a water-in-oil-in-water emulsion, preferably a water-in-oil-in-water emulsion, wherein said emulsion comprises:

an aqueous phase, wherein the amount of the aqueous phase in the emulsion ranges from about 70 to 99% in weight to the total weight of the emulsion, preferably is of about 81.5% w/w or of about 86.5% w/w; and an oil phase, wherein the amount of the oil phase in the emulsion ranges from about 1 to about 30% in weight to the total weight of the emulsion, preferably is of about 18.5% w/w or of about 13.5% w/w;

wherein the aqueous phase comprises:

a phosphorothioate oligonucleotide, preferably in an amount ranging from about 0.01% to about 3% in weight to the total weight of the emulsion, preferably from about 0.04% to about 2% w/w and more preferably is of about 1.72% w/w or of about 0.086% w/w; or in an amount ranging from about 0.01% to about 3% in weight to the total weight of the aqueous phase of the emulsion, preferably from about 0.04% to about 2.5% w/w and more preferably is of about 2.11% w/w; and at least one agent comprising a group thiol, preferably in an amount ranging from about 0.5% to about 5% in weight to the total weight of the emulsion, preferably from about 1 to about 3% w/w, more preferably is of about 2% w/w; or in an amount ranging from about 0.5% to about 5% in weight to the total weight of the aqueous phase of the emulsion of the invention, preferably from about 1 to about 3% w/w, more preferably is of about 2.45% w/w; and at least one phosphate compound, preferably in an amount ranging from about 0.05% to about 2% in weight to the total weight of the emulsion, preferably from about 0.1% to about 1% w/w, more preferably from about 0.3% to about 0.7% w/w, even more preferably is of about 0.4-0.6% w/w; or in an amount ranging from about 0.01% to about 2% in weight to the total weight of the aqueous phase of the emulsion of the invention, preferably from about 0.1% to about 1% w/w, more preferably is of about 0.5% w/w; and optionally, a viscosity modifying agent, preferably in an amount ranging from about 0.01 to about 0.1% in weight to the total weight of the emulsion, more preferably of about 0.05% w/w, or ranging from about 0.01% to about 0.2% in weight to the weight of the aqueous phase, preferably of about 0.061% w/w; and optionally, urea, in an amount ranging from about 0.5 to about 20% in weight to the total weight of the emulsion, preferably of about 4% w/w, or ranging from about 0.5% to about 20% in weight to the weight of the aqueous phase, preferably of about 4.9% w/w; and the oil phase comprises:
an oil, preferably in an amount ranging from about 1 to about 20% in weight to the total weight of the emulsion, preferably of about 8% w/w, or ranging from about 25% to about 75% in weight to the total weight of the oil phase, preferably of about 43.2% w/w; and optionally, at least one emulsifying agent, preferably in an amount ranging from about 1 to about 10% in weight to the total weight of the emulsion, preferably of about 3.5% w/w, or ranging from about 5% to about 40% in weight to the total weight of the oil phase, preferably of about 18.9% w/w; and optionally a thickening agent, preferably in an amount ranging from about 0.1 to about 10% in weight to the total weight of the emulsion, preferably of about 2% w/w, or ranging from about 1% to about 30% in weight to the total weight of the oil phase, preferably of about 10.8% w/w; and optionally, an osmolality modifying agent, preferably in an amount ranging from about 0.5 to about 25% in weight to the total weight of the emulsion, preferably of about 5% w/w, or ranging from about 10% to about 45% in weight to the total weight of the oil phase, preferably of about 27% w/w.

In one embodiment, the composition of the invention is an oil-in-water emulsion or a water-in-oil-in-water emulsion, preferably a water-in-oil-in-water emulsion, wherein said emulsion comprises:
an aqueous phase, wherein the amount of the aqueous phase in the emulsion ranges from about 70 to 99% in weight to the total weight of the emulsion, preferably is of about 81.5% w/w or of about 86.5% w/w; and an oil phase, wherein the amount of the oil phase in the emulsion ranges from about 1 to about 30% in weight to the total weight of the emulsion, preferably is of about 18.5% w/w or of about 13.5% w/w;

wherein
the aqueous phase comprises:
a phosphorothioate oligonucleotide, preferably in an amount ranging from about 0.01% to about 3% in weight to the total weight of the emulsion, preferably from about 0.04% to about 2% w/w and more preferably is of about 1.72% w/w or of about 0.086% w/w; or in an amount ranging from about 0.01% to about 3% in weight to the total weight of the aqueous phase of the emulsion, preferably from about 0.04% to about 2.5% w/w and more preferably is of about 2.11% w/w; and at least one agent comprising a group thiol, preferably in an amount ranging from about 0.5% to about 5% in weight to the total weight of the emulsion, preferably from about 1 to about 3% w/w, more preferably is of about 2% w/w; or in an amount ranging from about 0.5% to about 5% in weight to the total weight of the aqueous phase of the emulsion of the invention, preferably from about 1 to about 3% w/w, more preferably is of about 2.45% w/w; and at least one phosphate compound, preferably in an amount ranging from about 0.05% to about 2% in weight to the total weight of the emulsion, preferably from about 0.1% to about 1% w/w, more preferably from about 0.3% to about 0.7% w/w, even more preferably is of about 0.4-0.6% w/w; or in an amount ranging from about 0.01% to about 2% in weight to the total weight of the aqueous phase of the emulsion of the invention, preferably from about 0.1% to about 1% w/w, more preferably is of about 0.5% w/w; and optionally, a viscosity modifying agent, preferably Carbopol® 980 NF; preferably in an amount ranging from about 0.01 to about 0.1% in weight to the total weight of the emulsion, more preferably of about 0.05% w/w, or ranging from about 0.01% to about 0.2% in weight to the weight of the aqueous phase, preferably of about 0.061% w/w; and optionally, a pH buffering agent, preferably NaOH, in an amount sufficient for providing a pH ranging from about 6 to about 8, preferably from about 6.8 to about 7.2, more preferably of about 7; such as, for example, in an amount ranging from about 0.1 to about 0.5% in weight to the total weight of the emulsion, preferably of about 0.29% w/w, or ranging from about 0.2% to about 0.5% in weight to the weight of the aqueous phase, preferably of about 0.35% w/w; and optionally, urea, in an amount ranging from about 0.5 to about 20% in weight to the total weight of the emulsion, preferably of about 4% w/w, or ranging from about 0.5% to about 20% in weight to the weight of the aqueous phase, preferably of about 4.9% w/w; and the oil phase comprises:
an oil, preferably MCT, more preferably Miglyol 812™, preferably in an amount ranging from about 1 to about 20% in weight to the total weight of the emulsion, preferably of about 8% w/w, or ranging from about 25% to about 75% in weight to the total weight of the oil phase, preferably of about 43.2% w/w; and optionally, at least one emulsifying agent, preferably a mixture of glyceryl stearate and of PEG-75; preferably in an amount ranging from about 1 to about 10% in weight to the total weight of the emulsion, preferably of about 3.5% w/w, or ranging from about 5% to about 40% in weight to the total weight of the oil phase, preferably of about 18.9% w/w; and optionally a thickening agent, preferably cetyl alcohol; preferably in an amount ranging from about 0.1 to about 10% in weight to the total weight of the emulsion, preferably of about 2% w/w, or ranging from about 1% to about 30% in weight to the total weight of the oil phase, preferably of about 10.8% w/w; and optionally, an osmolality modifying agent, preferably glycerol; preferably in an amount ranging from about 0.5 to about 25% in weight to the total weight of the emulsion, preferably of about 5% w/w, or ranging from about 10% to about 45% in weight to the total weight of the oil phase, preferably of about 27% w/w.

In one embodiment, the composition of the invention is an oil-in-water emulsion or a water-in-oil-in-water emulsion, preferably a water-in-oil-in-water emulsion, wherein said emulsion comprises:

an aqueous phase, wherein the amount of the aqueous phase in the emulsion ranges from about 70 to 99% in weight to the total weight of the emulsion, preferably is of about 81.5% w/w or of about 86.5% w/w; and an oil phase, wherein the amount of the oil phase in the emulsion ranges from about 1 to about 30% in weight to the total weight of the emulsion, preferably is of about 18.5% w/w or of about 13.5% w/w;

wherein the aqueous phase comprises:
  a phosphorothioate oligonucleotide, preferably in an amount ranging from about 0.01% to about 3% in weight to the total weight of the emulsion, preferably from about 0.04% to about 2% w/w and more preferably is of about 1.72% w/w or of about 0.086% w/w; or in an amount ranging from about 0.01% to about 3% in weight to the total weight of the aqueous phase of the emulsion, preferably from about 0.04% to about 2.5% w/w and more preferably is of about 2.11% w/w; and at least one agent comprising a group thiol, preferably in an amount ranging from about 0.5% to about 5% in weight to the total weight of the emulsion, preferably from about 1 to about 3% w/w, more preferably is of about 2% w/w; or in an amount ranging from about 0.5% to about 5% in weight to the total weight of the aqueous phase of the emulsion of the invention, preferably from about 1 to about 3% w/w, more preferably is of about 2.45% w/w; and at least one phosphate compound, preferably in an amount ranging from about 0.05% to about 2% in weight to the total weight of the emulsion, preferably from about 0.1% to about 1% w/w, more preferably from about 0.3% to about 0.7% w/w, even more preferably is of about 0.4-0.6% w/w; or in an amount ranging from about 0.01% to about 2% in weight to the total weight of the aqueous phase of the emulsion of the invention, preferably from about 0.1% to about 1% w/w, more preferably is of about 0.5% w/w; and optionally, a viscosity modifying agent, preferably Carbopol® 980 NF; preferably in an amount ranging from about 0.01 to about 0.1% in weight to the total weight of the emulsion, more preferably of about 0.05% w/w, or ranging from about 0.01% to about 0.2% in weight to the weight of the aqueous phase, preferably of about 0.061% w/w; and optionally, urea, in an amount ranging from about 0.5 to about 20% in weight to the total weight of the emulsion, preferably of about 4% w/w, or ranging from about 0.5% to about 20% in weight to the weight of the aqueous phase, preferably of about 4.9% w/w; and the oil phase comprises:
  an oil, preferably MCT, more preferably Miglyol 812™, preferably in an amount ranging from about 1 to about 20% in weight to the total weight of the emulsion, preferably of about 8% w/w, or ranging from about 25% to about 75% in weight to the total weight of the oil phase, preferably of about 43.2% w/w; and optionally, at least one emulsifying agent, preferably a mixture of glyceryl stearate and of PEG-75; preferably in an amount ranging from about 1 to about 10% in weight to the total weight of the emulsion, preferably of about 3.5% w/w, or ranging from about 5% to about 40% in weight to the total weight of the oil phase, preferably of about 18.9% w/w; and optionally a thickening agent, preferably cetyl alcohol; preferably in an amount ranging from about 0.1 to about 10% in weight to the total weight of the emulsion, preferably of about 2% w/w, or ranging from about 1% to about 30% in weight to the total weight of the oil phase, preferably of about 10.8% w/w; and optionally, an osmolality modifying agent, preferably glycerol; preferably in an amount ranging from about 0.5 to about 25% in weight to the total weight of the emulsion, preferably of about 5% w/w, or ranging from about 10% to about 45% in weight to the total weight of the oil phase, preferably of about 27% w/w.

Also included within the scope of this invention are preserved compounds which increase in viscosity upon administration to the eye. Examples of such compounds include "gelling polysaccharides", disclosed in U.S. Pat. No. 5,212,162, which is incorporated in its entirety herein by reference. Also disclosed in this patent are ophthalmic formulations containing carrageenans and furcellarans which are administered as partially gelled liquids which gel upon instillation into the eye. Additionally, U.S. Pat. Nos. 4,136,173, 4,136,177, and 4,136,178, disclose the use of therapeutic compositions containing xanthan gum and locust bean gum which are delivered in liquid form to the eye and which gel upon instillation. U.S. Pat. No. 4,861,760 discloses ophthalmological compositions containing gellan gum which are administered to the eye as non-gelled liquids and which gel upon instillation. Each of these four patents is incorporated in its entirety herein by reference. Also within the scope of this invention are preserved oils, ointments, gels and the like.

The present invention also relates to a method for preventing and/or inhibiting the degradation of a phosphorothioate oligonucleotide in a composition comprising at least one fatty acid and/or at least one emulsifying agent and subjected to steam sterilization, preferably to autoclaving, wherein said method comprises adding at least one phosphate compound and/or at least one agent comprising a thiol group within the composition.

The present invention also relates to a method for obtaining a sterile composition comprising a phosphorothioate oligonucleotide and at least one fatty acid and/or at least one emulsifying agent, preferably a sterile ophthalmic composition, wherein said phosphorothioate oligonucleotide is stable within the sterile composition, wherein said method comprises adding at least one phosphate compound and/or at least one agent comprising a thiol group within the composition.

In one embodiment, the method according to the present invention comprises or consists of mixing a bulk emulsion and a phosphorothioate solution.

In one embodiment, the method according to the present invention comprises or consists of mixing a bulk emulsion and a phosphorothioate solution, wherein:
- the percentage of the bulk emulsion ranges from about 60% to about 99% in weight to the total weight of the composition, preferably from about 75% to about 85% w/w, more preferably is of about 80% w/w; and wherein
- the percentage of the phosphorothioate solution ranges from about 1% to about 40% in weight to the total weight of the composition, preferably from about 15% to about 25% w/w, more preferably is of about 20% w/w.

In one embodiment, the bulk emulsion is an emulsion such as a water-in-oil bulk emulsion, an oil-in-water bulk emulsion, a water-in-oil-in-water bulk emulsion or any multiphasic bulk emulsion. Preferably, the bulk emulsion is a water-in-oil-in-water bulk emulsion.

In one embodiment, the bulk emulsion is cationic. In another embodiment, the bulk emulsion is anionic.

In one embodiment, the bulk emulsion according to the present invention comprises an aqueous phase and an oil phase dispersed in the aqueous phase, wherein:
- the percentage of the aqueous phase ranges from about 70% to about 99% in weight to the total weight of the bulk emulsion, preferably from about 75% to about 90% w/w, more preferably is of about 83.125% w/w; and wherein
- the percentage of the oil phase ranges from about 1% to about 35% in weight to the total weight of the bulk emulsion, preferably from about 7.5% to about 27.5% w/w or from about 12.5% to about 22.5% w/w, more preferably is of about 16.875%.

In one embodiment, the oil phase of the bulk emulsion may comprise an oil, an emulsifying agent, a thickening agent, and/or an osmolality modifying agent, as described hereinabove.

In one embodiment, the aqueous phase of the bulk emulsion may comprise a viscosity modifying agent, a pH buffering agent, and/or urea, as described hereinabove.

In one embodiment of the invention, the amount of the oil in the bulk emulsion, if present, ranges from about 1 to about 20% in weight to the total weight of the bulk emulsion, preferably from about 5% to about 10% w/w, more preferably is of about 10% w/w.

In one embodiment of the invention, the amount of emulsifying agent in the bulk emulsion, if present, ranges from about 1% to about 10% in weight to the total weight of the bulk emulsion, preferably from about 2.5% to about 6.5% w/w, more preferably is of about 4.375% w/w.

In one embodiment of the invention, the amount of thickening agent in the bulk emulsion, if present, ranges from about 0.1% to about 10% in weight to the total weight of the bulk emulsion, preferably from about 1% to about 5% w/w, more preferably is of about 2.5% w/w.

In one embodiment of the invention, the amount of osmolality modifying agent in the bulk emulsion, if present, ranges from about 0.5% to about 20% in weight to the total weight of the bulk emulsion, preferably from about 2% to about 10% w/w, more preferably is of about 6.25% w/w.

In one embodiment of the invention, the amount of the viscosity modifying agent in the emulsion, if present, ranges from about 0.01% to about 0.25% in weight to the total weight of the bulk emulsion, preferably from about 0.025% to about 0.1% w/w, more preferably is of about 0.0625% w/w.

In one embodiment of the invention, the amount of the viscosity modifying agent in the emulsion, if present, ranges from about 0.01% to about 0.25% in weight to the total weight of the bulk emulsion, preferably from about 0.075% to about 0.175% w/w, more preferably is of about 0.125% w/w.

In one embodiment, the oil-in-water bulk emulsion described hereinabove further comprises an aqueous phase inside the oil droplets dispersed in the aqueous phase, and is therefore a water-in-oil-in-water bulk emulsion.

In one embodiment, the phosphorothioate solution comprises at least one phosphorothioate oligonucleotide and/or at least one agent comprising a thiol group and/or at least one phosphate compound.

In one embodiment, the method of the invention comprises or consists of (i) mixing the ingredients of the aqueous phase, to the exclusion of the at least one agent comprising a thiol group, of the at least one phosphate compound and/or of the phosphorothioate oligonucleotide, (ii) mixing the ingredients of the oil phase, and (iii) mixing the oil and aqueous phases to obtain a bulk emulsion.

In one embodiment, the method of the invention comprises (i) mixing the ingredients of the oil phase, (ii) mixing the ingredients of the aqueous phase, to the exclusion of the at least one agent comprising a thiol group, of the at least one phosphate compound and/or of the phosphorothioate oligonucleotide, and (iii) mixing the oil and aqueous phases to obtain a bulk emulsion.

In one embodiment, the mixing step(s) of the method of the invention is/are carried out by magnetic stirring. In one embodiment, the mixing step(s) of the method of the invention is/are carried out by heating, preferably by heating to a temperature ranging from about 40° to 100° C., preferably at about 70° C. In one embodiment, the mixing step(s) of the method of the invention is/are carried out by magnetic sitting and heating.

In one embodiment, the pH of the bulk emulsion is constant, and ranges from about 6 to about 8, preferably from about 6.8 to about 7.2, more preferably is of about 7.

In one embodiment, the pH of the phosphorothioate solution is constant, and ranges from about 6.5 to about 8.5, preferably from about 7 to about 8, more preferably is of about 7.5.

In one embodiment, the pH of the sterile composition, preferably of the emulsion, according to the present invention is constant, and ranges from about 6 to about 8, preferably from about 6.8 to about 7.2, more preferably is of about 7. In one embodiment, said pH of the sterile composition is sterile overtime, such as, for example, for 1 week, 2 weeks, 1 month, 2 months, 3 months, 6 months or more, at a temperature ranging from about 5 to about 40° C., more preferably at a temperature of about 5° C. or of about 17 to 25° C.

In one embodiment, the methods of the invention further comprise a step of sterilization of the bulk emulsion. In one embodiment, the sterilization of the bulk emulsion is carried out by steam heating, such as autoclaving.

In one embodiment, the sterilization step, preferably the autoclaving step comprises heating the bulk emulsion, at a temperature ranging from about 100° C. to about 130° C., preferably at a temperature ranging from about 116° C. to about 125° C. and more preferably at about 121° C.; for a period ranging from about 10 to about 30 minutes, preferably from about 15 to about 25 minutes and more preferable of about 20 minutes. Preferably, the autoclaving step comprises heating the composition, preferably the emulsion, at about 121° C. for about 20 minutes. In one embodiment, the autoclaving step is carried out under a pressure ranging from about 0.5 bar to about 1.5 bar, preferably from about 0.8 bar to about 1.2 bar, and more preferably of about 1 bar.

In one embodiment, the methods of the invention further comprise a step of preparing a phosphorothioate solution, by mixing at least one phosphorothioate oligonucleotide and/or at least one agent comprising a thiol group and/or at least one phosphate compound.

In one embodiment, the methods of the invention further comprise a step of sterilizing the phosphorothioate solution.

In one embodiment, the phosphorothioate solution sterilization step comprises filtering the solution, preferably using a filter with a size ranging from about 0.2 µm to about 0.8 µm, preferably from about 0.4 µm to about 0.5 µm, and more preferably through a 0.45 µm filter.

In one embodiment, the methods of the invention further comprise a step of mixing the sterile bulk emulsion and the sterile phosphorothioate solution, preferably under sterile conditions.

In one embodiment, the method according to the present invention may comprise or consist of the following steps:
preparing and/or mixing the oil phase and the aqueous phase as described herein above, including the at least one fatty acid and/or at least one emulsifying agent, to the exclusion of the at least one agent comprising a thiol group, of the at least one phosphate compound and/or of the phosphorothioate oligonucleotide, to obtain a bulk emulsion;
sterilizing the bulk emulsion resulting from the previous step, preferably by steam sterilization, such as by autoclaving; and
adding a phosphorothioate solution, preferably a sterile phosphorothioate solution, to the sterile bulk emulsion, preferably under sterile conditions, said phosphorothioate solution comprising a phosphorothioate oligonucleotide, at least one phosphate compounds and/or at least one agent comprising a thiol group.

Thus, in one embodiment, the method of the invention comprises or consists of the steps of:
mixing the ingredients of the aqueous phase of the bulk emulsion, to the exclusion of the at least one agent comprising a thiol group, of the at least one phosphate compound and/or of the phosphorothioate oligonucleotide;
mixing the ingredients of the oil phase of the bulk emulsion;
mixing the oil and aqueous phases resulting from the previous steps to obtain a bulk emulsion;
sterilizing the bulk emulsion;
preparing a phosphorothioate solution, by mixing at least one phosphorothioate oligonucleotide and/or at least one agent comprising a thiol group and/or at least one phosphate compound;
sterilizing the phosphorothioate solution;
mixing the sterile bulk emulsion and the sterile phosphorothioate solution, preferably under sterile conditions.

In one alternative embodiment, the method of the invention comprises or consists of the steps of:
mixing the ingredients of the aqueous phase of the bulk emulsion, to the exclusion of the at least one agent comprising a thiol group, of the at least one phosphate compound and/or of the phosphorothioate oligonucleotide;
mixing the ingredients of the oil phase of the bulk emulsion;
mixing the oil and aqueous phases resulting from the previous steps to obtain a bulk emulsion;
sterilizing the bulk emulsion;
preparing a phosphorothioate solution, by mixing at least one agent comprising a thiol group and/or at least one phosphate compound, to the exclusion of the at least one phosphorothioate oligonucleotide;
sterilizing the phosphorothioate solution;
adding the at least one phosphorothioate oligonucleotide to the phosphorothioate solution, preferably under sterile conditions;
mixing the sterile bulk emulsion and the sterile phosphorothioate solution, preferably under sterile conditions.

According to one embodiment, the steps of the method of the invention described above can be carried out in any order.

In one embodiment, the phosphorothioate oligonucleotide is stable in the composition of the invention. In other words, in one embodiment, the composition of the invention prevents degradation of the phosphorothioate oligonucleotide.

As used herein, the term "stable" refers to the phosphorothioate oligonucleotide which remains within about 20% or less by weight of the original amount when incubated at the recited temperature for the recited amount of time, preferably within about 15% w/w, about 10% w/w, about 9% w/w, about 8% w/w, about 7% w/w, about 6% w/w, about 5% w/w, about 4% w/w, about 3% w/w, about 2% w/w, about 1% w/w or less.

Figure 2:
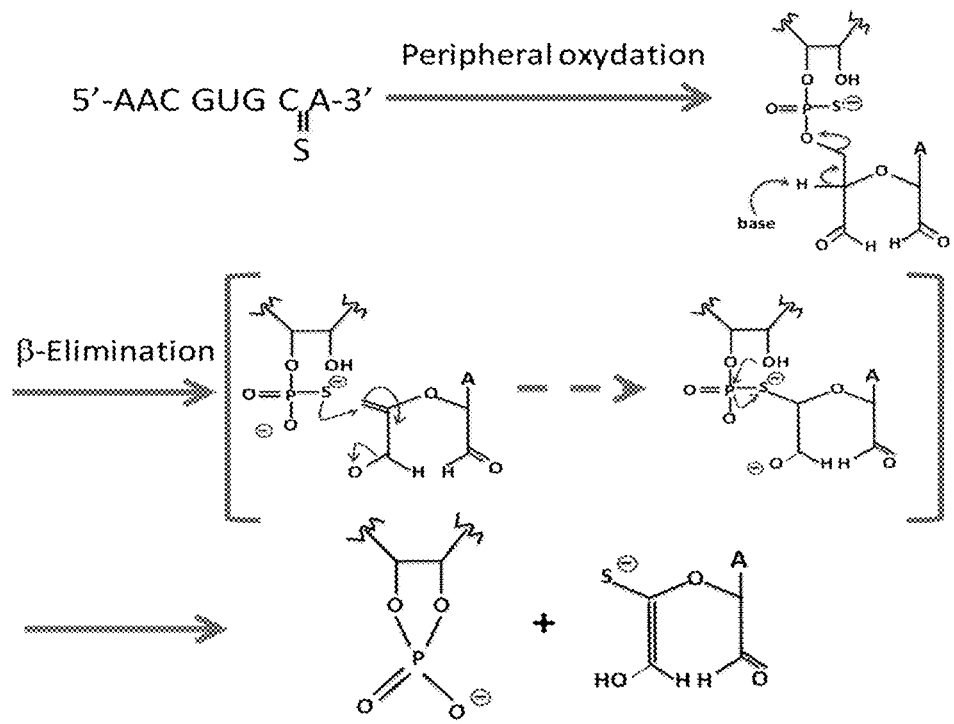
FIG. 2 is a scheme showing the sequential peripheral oxidation of phosphorothioate-derived oligonucleotides followed by β-elimination reaction.

In one embodiment, the degradation of the phosphorothioate oligonucleotide comprises sequential oxidation provoked by the attack of highly reactive entities liberated from the at least one fatty acid and/or from the at least one emulsifying agent due to the high temperature of steam sterilization, and subsequent β-elimination as shown in FIGS. 1 and 2.

The stability of the phosphorothioate oligonucleotide can be assessed, after extraction of the oligonucleotide from the composition, by ion-exchange chromatography (IEX-HPLC) coupled to UV detection. Examples of chromatographic conditions that may be used include, but are not limited to, the following conditions:
pre-columns and columns—DIONEX DNAS Pack pa-100;
mobile phases:
A: NaOH 10 mM in water;
B: NaOH 10 mM and $NaClO_4$ 0.375 M.

The stability of the phosphorothioate oligonucleotide can also be assessed by reverse-phase high-performance liquid chromatography (RP-HPLC) coupled to UV detection. Examples of chromatographic conditions that may be used include, but are not limited to, the following conditions:

column: Waters Acquity UPLC OST BEH C18 2.1×50 mm, 1.7 µm bead size;
mobile phases:
A: Water;
B: 17.2 mM triethanolamine, 200 mM hexafluoroisopropanol in water;
C: MeOH.

In one embodiment, the stability of the phosphorothioate oligonucleotide is expressed as a percentage assay value. Percentage assays are techniques well-known to the skilled artisan.

In one embodiment, the phosphorothioate oligonucleotide is considered stable when the percentage assay value remains within about 20% or less of the original percentage assay value when incubated at the recited temperature for the recited amount of time, preferably within about 15%, about 10%, about 9%, about 8%, about 7%, about 6%, about 5%, about 4%, about 3%, about 2%, about 1% or less.

In one embodiment of the invention, the phosphorothioate oligonucleotide is stable for at least about 1 day, preferably at least about 1 week, more preferably for at least about 1 month or more, such as 2, 3, 4, 5, 6, 12, 24 months or more at room temperature (i.e., a temperature ranging from about 15 to about 25° C., preferably at a temperature of about 20° C.) in the composition of the invention.

In another embodiment of the invention, the phosphorothioate oligonucleotide is stable for at least about 10 minutes, preferably at least about 1 hour, more preferably for at least about 5, 6, 7, 8, 9, 10, 12, 24, 48 hours or more at a temperature of at least about 40° C., preferably of at least about 50° C., more preferably of about 60° C.

In another embodiment of the invention, the phosphorothioate oligonucleotide is stable for at least about 1, 2, 3, 4, 5, 6, 7, 10, 14, 21, 28 days, 1 month, 2, 3, 4, 5, 6 months or more at a temperature of at least about 40° C.

In one embodiment, less than about 10%, preferably less than about 5%, preferably less than about 4%, 3%, 2%, 1% of the initial amount of phosphorothioate oligonucleotide is degraded after 1 month of incubation at 5° C. In one embodiment, less than about 10%, preferably less than about 5%, preferably less than about 4%, 3%, 2%, 1% of the initial amount of phosphorothioate oligonucleotide is degraded after 2 months of incubation at 5° C. In one embodiment, less than about 10%, preferably less than about 5%, preferably less than about 4%, 3%, 2%, 1% of the initial amount of phosphorothioate oligonucleotide is degraded after 3 months of incubation at 5° C. In one embodiment, less than about 10%, preferably less than about 5%, preferably less than about 4%, 3%, 2%, 1% of the initial amount of phosphorothioate oligonucleotide is degraded after 6 months of incubation at 5° C.

In one embodiment, less than about 10%, preferably less than about 5%, preferably less than about 4%, 3%, 2%, 1% of the initial amount of phosphorothioate oligonucleotide is degraded after 2 weeks of incubation at 25° C. In one embodiment, less than about 10%, preferably less than about 5%, preferably less than about 4%, 3%, 2%, 1% of the initial amount of phosphorothioate oligonucleotide is degraded after 1 month of incubation at 25° C. In one embodiment, less than about 10%, preferably less than about 5%, preferably less than about 4%, 3%, 2%, 1% of the initial amount of phosphorothioate oligonucleotide is degraded after 2 months of incubation at 25° C. In one embodiment, less than about 10%, preferably less than about 5%, preferably less than about 4%, 3%, 2%, 1% of the initial amount of phosphorothioate oligonucleotide is degraded after 3 months of incubation at 25° C. In one embodiment, less than about 20%, preferably less than about 15%, preferably less than about 10%, of the initial amount of phosphorothioate oligonucleotide is degraded after 6 months of incubation at 25° C.

In one embodiment, less than about 10%, preferably less than about 5%, preferably less than about 4%, 3%, 2%, 1% of the initial amount of phosphorothioate oligonucleotide is degraded after 2 weeks of incubation at 40° C. In one embodiment, less than about 10%, preferably less than about 9%, 8%, 7%, 6%, 5%, 4%, 3%, 1% 2%, of the initial amount of phosphorothioate oligonucleotide is degraded after 1 month of incubation at 40° C. In one embodiment, less than about 15%, preferably less than about 10%, preferably less than about 9%, 8%, 7%, 6%, 5%, 4%, 3%, 2%, 1% of the initial amount of phosphorothioate oligonucleotide is degraded after 2 months of incubation at 40° C. In one embodiment, less than about 25%, preferably less than about 20%, preferably less than about 19%, 18%, 17%, 16%, 15%, 14%, 13%, 12%, 11%, 10%, 9%, 8%, 7%, 6%, 5%, 4%, 3%, 2%, 1% of the initial amount of phosphorothioate oligonucleotide is degraded after 3 months of incubation at 40° C.

The present invention further relates to a composition obtained by, or obtainable by, the methods of the invention.

In one embodiment, the phosphorothioate oligonucleotide comprised in the composition obtained by, or obtainable by, the method of the invention is stable. In other words, in one embodiment, the composition obtained by, or obtainable by, the methods of the invention prevents degradation of the phosphorothioate oligonucleotide.

The stability of the phosphorothioate oligonucleotide comprised in the composition obtained by, or obtainable by, the method of the invention can be assessed, after extraction of the oligonucleotide from the emulsion, by ion-exchange chromatography (IEX-HPLC) coupled to UV detection or by reverse-phase high-performance liquid chromatography (RP-HPLC) coupled to UV detection, as described hereinabove.

In one embodiment, the phosphorothioate oligonucleotide comprised in the composition obtained by, or obtainable by, the method of the invention is stable for at least about 1 day, preferably at least about 1 week, more preferably for at least about 1 month or more, such as 2, 3, 4, 5, 6, 12, 24 months or more at room temperature (i.e., a temperature ranging from about 15 to about 25° C., preferably at a temperature of about 20° C.) in the composition of the invention.

In one embodiment, the phosphorothioate oligonucleotide comprised in the composition obtained by, or obtainable by, the method of the invention is stable for at least about 10 minutes, preferably at least about 1 hour, more preferably for at least about 5, 6, 7, 8, 9, 10, 12, 24, 48 hours or more at a temperature of at least about 40° C., preferably of at least about 50° C., more preferably of about 60° C.

In one embodiment of the invention, the phosphorothioate oligonucleotide comprised in the composition obtained by, or obtainable by, the method of the invention is stable for at least about 1, 2, 3, 4, 5, 6, 7, 10, 14, 21, 28 days, 1 month, 2, 3, 4, 5, 6 months or more at a temperature of at least about 40° C.

In one embodiment, the composition of the invention or the composition obtained by, or obtainable by the methods of the invention, is a pharmaceutical composition, and comprises at least one pharmaceutically acceptable excipient.

The present invention further relates to a pharmaceutical composition comprising the composition of the invention or the composition obtained by, or obtainable by, the methods of the invention, and at least one pharmaceutically acceptable excipient.

Examples of pharmaceutically acceptable excipients include but are not limited to water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene- polyoxypropylene- block polymers, polyethylene glycol and wool fat.

In addition, pharmaceutically acceptable excipients may comprise some excipients, such as, for example, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextrose, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

The present invention further relates to a medicament comprising the composition of the invention or the composition obtained by, or obtainable by, the methods of the invention.

The composition, pharmaceutical composition and/or medicament of the invention may be formulated into a variety of topically or injectable administrable compositions. Examples of such formulations include, but are not limited to, emulsions, gels, ointments, micelles or eye drops.

In one embodiment, the composition is formulated in accordance with routine procedures as a composition, pharmaceutical composition or medicament adapted for topical administration (in particular for topical administration to the eye) or for injection (in particular for intravitreal injection, subconjuctival injection, injection into the conjunctival sac, sub-tenon injections, retrobulbar injection, suprachoroidal injection, or intracameral injection) to human beings.

In one embodiment of the invention, said composition, pharmaceutical composition or medicament of the invention is packaged in the form of unit dose. Examples of unit doses that may be used include, but are not limited to, a container capable of dispensing eye drops such as common manual bulb-operated pipette or small squeeze bottle with a dropper tip; a container to which a device for the placement of eye drops may be applied; a container capable of atomizing drops or droplets and a disposable syringe.

It will be understood that the total daily usage of the composition, pharmaceutical composition and medicament of the present invention will be decided by the attending physician within the scope of sound medical judgment. The specific therapeutically effective amount for any particular patient will depend upon a variety of factors including the disorder being treated and the severity of the disorder; activity of the specific phosphorothioate oligonucleotide employed; the specific composition employed, the age, body weight, general health, sex and diet of the subject; the time of administration, route of administration, and rate of excretion of the specific phosphorothioate oligonucleotide employed; the duration of the treatment; drugs used in combination or coincidental with the specific phosphorothioate oligonucleotide employed; and like factors well known in the medical arts. For example, it is well within the skill of the art to start doses of a therapeutic compound at levels lower than those required to achieve the desired therapeutic effect and to gradually increase the dosage until the desired effect is achieved.

The present invention further relates to the composition, pharmaceutical composition or medicament of the invention for treating or for use in the treatment of an angiogenic disorder in a subject in need thereof, wherein the composition, pharmaceutical composition or medicament preferably comprises an IRS-1 inhibitor as described hereinabove.

Angiogenesis is a fundamental process by means of which new blood vessels are formed. Angiogenesis is essential in multiple normal physiological phenomena such as reproduction, development and even wound healing. Angiogenic disorder refers to a pathological neovascularization as is occurring in a number of diseases, where the pathological neovascularization is linked to the invasion of tissues and organs by neovessels. Examples of angiogenic disorders include, but are not limited to, ocular neovascular diseases (such as, for example, ischemic retinopathy, diabetic retinopathy, retinopathy of prematurity, retinal vein occlusions, age-related macular degeneration, corneal neovascularisation, neovascular glaucoma), atherosclerosis, arthritis, psoriasis, obesity, cancer and Alzheimer's disease. In one embodiment of the invention, the angiogenic disorder is an ocular angiogenic disease.

According to an embodiment, the ocular angiogenic disease is associated with retinal, peripheral retinal and/or choroidal neovascularization. Examples of such angiogenic diseases include, but are not limited to uveitis, choroiditis, choroidal vasculopathy, hypersensitive retinopathy, retinochoroiditis, chorioretinitis, retinal angiomatosis, retinal degeneration, macular degeneration, AMD, retinal detachment, retinal neovascularisation, proliferative vitreoretinopathy, retinopathy of prematurity (ROP), central serous chorioretinopathy, diabetic retinopathy, posterior segment trauma, retinal vascular pathologies, retinal telangiectasia, endophthalmitis, macular edema, radiation-induced retinopathy, cystoid macular edema, diabetic retinopathy, inflammatory pathologies of the retina, sickle cell anemia, sickle cell retinopathy, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, systemic pathologies with implications for the retina, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

According to an embodiment, the ocular angiogenic disease is associated with corneal neovascularization. Examples of such angiogenic diseases include, but are not limited to diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, Sjogren's syndrome, acne rosacea, phlyctenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease and pemphigoid, radial keratotomy.

According to an embodiment, the ocular angiogenic disease is selected from the group comprising diseases associated with rubeosis (neovascularization of the angle) and diseases caused by the abnormal proliferation of fibrovascular or fibrous tissue including all forms of proliferative vitreoretinopathy, whether or not associated with diabetes.

The present invention further relates to a method for treating an angiogenic disorder in a subject in need thereof, wherein the method comprises administering to the subject the composition, pharmaceutical composition or medicament of the invention, wherein said composition, pharmaceutical composition or medicament preferably comprises an IRS-1 inhibitor as described hereinabove.

The present invention further relates to a method for inhibiting angiogenesis in a subject in need thereof, wherein the method comprises administering to the subject the composition, pharmaceutical composition or medicament of the invention, wherein said composition, pharmaceutical composition or medicament preferably comprises an IRS-1 inhibitor as described hereinabove.

The present invention further relates to a method for preventing, stabilizing and/or inhibiting lymph or blood vascularization or corneal angiogenesis in a subject in need thereof, wherein the method comprises administering to the subject the composition, pharmaceutical composition or medicament of the invention, wherein said composition, pharmaceutical composition or medicament preferably comprises an IRS-1 inhibitor as described hereinabove.

The present invention further relates to a method for preventing or stabilizing neovascularization in a subject in need thereof, wherein the method comprises administering to the subject the composition, pharmaceutical composition or medicament of the invention, wherein said composition, pharmaceutical composition or medicament preferably comprises an IRS-1 inhibitor as described hereinabove.

In one embodiment, a therapeutically effective amount of the composition, pharmaceutical composition or medicament of the invention is administered to the subject.

In one embodiment of the invention, the amount of said phosphorothioate antisense oligonucleotide inhibitor of IRS-1 to be administrated per eye per day ranges from about 8 µg to about 40 µg, preferably from about 10 µg to about 35 µg, preferably from about 12 µg to about 30 µg, more preferably from about 14 µg to about 25 µg and even more preferably from about 16 µg to about 20 µg.

In one embodiment of the invention, the composition, pharmaceutical composition or medicament of the invention is to be administrated as drops of about 1 µL to about 1 mL, preferably from about 10 µL to about 100 more preferably of about 50 µL per eye. It is generally acknowledged that, when a pharmaceutical composition is administrated in the form of an eye drop i.e., 50 only about 10 µL may stay on the eye.

In one embodiment, one or two drops of the composition of the invention are administered per eye per day.

In one embodiment of the invention, said pharmaceutical composition is to be administrated once, twice, three or more times a day. In one embodiment, said pharmaceutical composition is to be administrated once a day. In another embodiment, said pharmaceutical composition is to be administrated twice a day, preferably in the morning and in the evening.

In one embodiment of the invention, the amount of the phosphorothioate oligonucleotide, preferably of the IRS-1 antisense, to be administrated per eye per day ranges from about 20 µg to 100 µg, preferably from about 30 µg to about 90 µg, more preferably from about 40 µg to about 90 µg, even more preferably from about 50 µg to about 90 µg, still even more preferably from about 60 µg to about 90 µg, still even more preferably from about 70 µg to about 90 µg and still even more preferably from about 80 µg to about 90 µg.

In one embodiment, the amount of the phosphorothioate oligonucleotide, preferably of the
IRS-1 antisense, to be administrated per eye per day ranges from about 40 µg to about 50 µg, preferably is of about 43 µg, corresponding for example, to about 20 µg to 25 µg per drop with an administration of 2 drops per eye per day.

In another embodiment, the amount of the phosphorothioate oligonucleotide, preferably of the IRS-1 antisense, to be administrated per eye per day ranges from about 80 µg to about 100 µg, preferably is about 86 µg, corresponding for example, to about 40 µg to 50 µg per drop with an administration of 2 drops per eye per day.

In said embodiment, the pharmaceutical composition is preferably in the form of a unit dose for administering from about 80 µg to 100 µg, preferably about 86 µg, of said phosphorothioate oligonucleotide per eye per day.

For example, two drops of 50 µL, of a composition comprising from about 0.80 mg/mL to about 1 mg/mL of said antisense oligonucleotide may be administrated per eye in one time to the subject in need thereof. In another example, one drop of 50 µL, of a composition comprising from about 1.60 mg/mL to about 2 mg/mL of said antisense oligonucleotide may be administrated per eye to the subject in need thereof.

In another example, one drop of 50 µL, of a composition comprising from about 0.80 mg/mL to about 1 mg/mL of said phosphorothioate oligonucleotide is administrated per eye twice a day to the subject in need thereof.

The present invention further relates to a kit, for performing the methods of the present invention.

As used herein, the term "kit" refers to any manufacture (e.g., a package or at least one container) comprising different reagents necessary for carrying out the methods according to the present invention, packed so as to allow their transport and storage. A kit may be promoted, distributed, or sold as a unit for performing the methods of the present invention. Furthermore, any or all of the kit reagents may be provided within containers that protect them from the external environment, such as in sealed and sterile containers. The kit may also contain a package insert describing the kit and methods for its use.

In one embodiment, the kit of the present invention comprises:
- a phosphorothioate oligonucleotide; and/or
- at least one agent comprising a group thiol; and/or
- at least one phosphate compound; and/or
- optionally, a viscosity modifying agent, preferably Carbopol® 980 NF; and/or
- optionally, a pH buffering agent, preferably NaOH; and/or
- optionally, urea; and/or
- an oil, preferably MCT, more preferably Miglyol 812™; and/or
- optionally, at least one emulsifying agent, preferably a mixture of glyceryl stearate and of PEG-75 such as Gelot 64®; and/or
- optionally, a thickening agent, preferably cetyl alcohol; and/or
- optionally, an osmolality modifying agent, preferably glycerol.

In one embodiment, the kit of the present invention comprises:
- a bulk emulsion, preferably a sterile bulk emulsion, as described hereinabove; and
- a phosphorothioate solution, preferably a sterile phosphorothioate solution as described hereinabove.

In one embodiment, the kit of the present invention comprises:
- a bulk emulsion, preferably a sterile bulk emulsion, as described hereinabove;
- a phosphorothioate solution, preferably a sterile phosphorothioate solution, as described hereinabove, to the exclusion of the phosphorothioate oligonucleotide; and
- optionally, a phosphorothioate oligonucleotide.

In one embodiment, the phosphorothioate oligonucleotide comprised in the kit is an antisense oligonucleotide specific for IRS-1 (insulin receptor substrate-1), preferably an IRS-1 antisense phosphorothioate oligonucleotide comprising a sequence of at least 12 contiguous nucleotides of SEQ ID NO: 1. In one embodiment, the phosphorothioate oligonucleotide comprises or consists of the nucleic acid sequence SEQ ID NO: 2 or a function-conservative derivative thereof, such as any of SEQ ID NO: 3 to SEQ ID NO: 28.

BRIEF DESCRIPTION OF THE DRAWINGS

FIG. 1 is a scheme showing the sequential peripheral oxidation of phosphorothioate-derived oligonucleotides.

FIG. 2 is a scheme showing the sequential peripheral oxidation of phosphorothioate-derived oligonucleotides followed by β-elimination reaction.

Figure 3A:
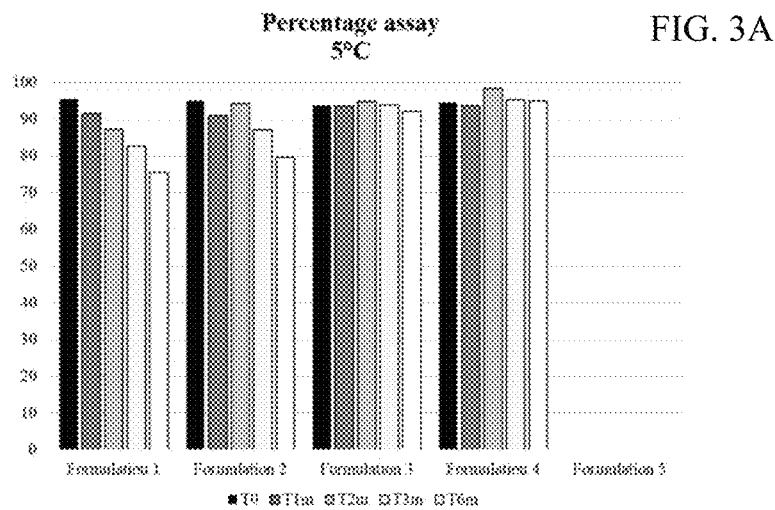
FIGS. 3A-3C are a set of histograms showing the percentage assay, i.e., the ratio of purities (intact GS-101 oligonucleotides) versus impurities (degraded GS-101 oligonucleotides), expressed as a percentage. Analysis were carried out on day 0 (T0), after 2 weeks (T2w), after one month (T1m), after 2 months (T2m), after 3 months (T3m) and after 6 months (T6m).
Figure 3B:
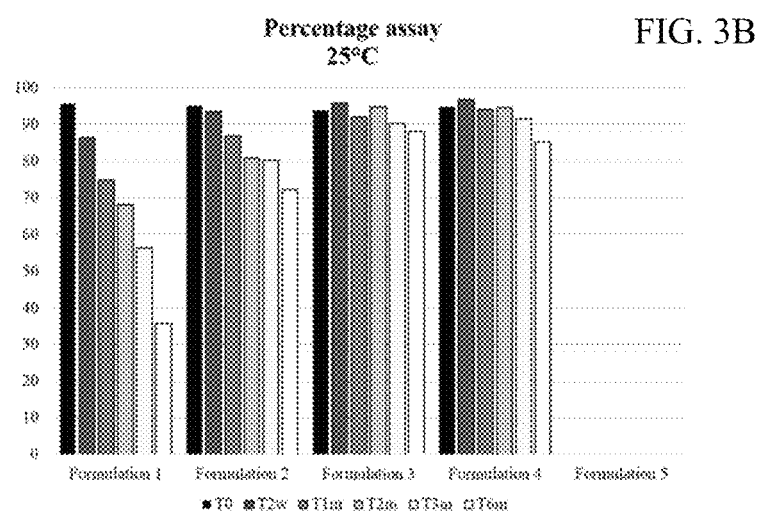
Figure 3C:
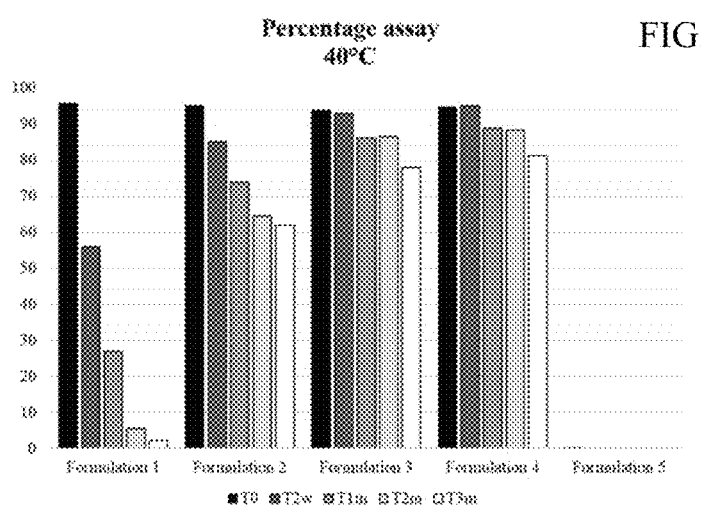

FIG. 3 is a set of histograms showing the percentage assay, i. e., the ratio of purities (intact GS-101 oligonucleotides) versus impurities (degraded GS-101 oligonucleotides), expressed as a percentage. Analysis were carried out on day 0 (T0), after 2 weeks (T2w), after one month (T1m), after 2 months (T2m), after 3 months (T3m) and after 6 months (T6m). FIG. 3A reports the percentage assay results of various formulations of the GS-101 sterile emulsion, incubated at 5° C.; FIG. 3B reports the same results for emulsions incubated at 25° C.; FIG. 3C reports the same results for emulsions incubated at 40° C.

EXAMPLES

The present invention is further illustrated by the following examples.

Example 1

Accelerated Stability Study of GS-101 in Presence of Phosphate

The accelerated stability study of GS-101 is reported in this example. A composition containing 0.86 mg GS-101/g emulsion was evaluated in 7 different formulations, comprising phosphate compounds and/or an antioxidant, such as an agent comprising a thiol group. These formulations were kept at different storage conditions, and the stability of GS-101 in the different formulations was evaluated by reversed-phase high-performance liquid chromatography (RP-HPLC).

Materials and Methods
Preparation of the Sterile Bulk Emulsion

8% w/w* of Miglyol 812™, 3.5% w/w* of Gelot 64® and 2% w/w* of cetyl alcohol were mixed in a beaker. The beaker was then placed onto a magnetic stirrer-heater adjusted at 70° C. The resulting oil phase was solubilized and homogenized under continuous stirring (300 rpm) at 70° C. for 10 minutes.

Parallelly, 0.05% w/w* or 0.1% w/w* of Carbopol® 980NF (depending on the formulation as described below in Table 1) were dissolved in 70 mL of ultrapure water in a 100-mL beaker. The mixture was solubilized under magnetic stirring for at least 30 minutes and the pH was adjusted to 7 with 1 N NaOH solution. The resulting aqueous phase was then heated to 70° C.

* percentages are given in w/w of the total composition.

The prepared oil phase kept at 70° C. was gradually added to the prepared aqueous phase kept at 70° C., under stirring, at room temperature.

After cooling down to room temperature, the resulting bulk emulsion was autoclaved for 20 minutes at 121° C. under 1 bar pressure. The sterile bulk emulsions were kept under agitation until their cooling to room temperature.

Preparation of the GS-101 Sterile Emulsions 32 grams of sterile bulk emulsion were supplemented with 8 grams of a GS-101 solution.

Since the GS-101 solution has to be filtered twice before addition to the sterile bulk emulsion, 10 grams were prepared. These 10 grams can contain one or more of the following substances:
- 50 mg (0.1% w/w*) or 125 mg (0.25% w/w*) of N-acetylcysteine (NAC), an agent containing a thiol group (dissolved in 2 M NaOH);
- 50 mg (0.1% w/w*) or 125 mg (0.25% w/w*) of sodium metabisulfite, an agent which does not contain a thiol group;
- 155 mg of $Na_2HPO_4.12H_2O$ and 43.8 mg of $NaH_2PO_4.H_2O$ (15 mM phosphate final in the total composition);
- 43 mg (0.086% w/w*) of GS-101 having the sequence SEQ ID NO: 2 (5'-TCTCCGGAGGGCTCGC-CATGCTGCT-3').

* percentages are given in w/w of the total composition.
The various composition formulations are detailed in Table 1 below.

TABLE 1

| Formulation number | % of Carbopol ® 980NF (w/w) | 15 mM phosphate buffer? | Aeration with N$_2$-gas? | % and type of antioxidant (w/w) |
|---|---|---|---|---|
| 1 | 0.05 | No | No | No |
| 2 | 0.1 | Yes | No | No |
| 3 | 0.1 | Yes | Yes | No |
| 4 | 0.1 | Yes | No | 0.1% NAC |
| 5 | 0.1 | Yes | No | 0.25% NAC |
| 6 | 0.1 | Yes | No | 0.1% Na-metabisulfite |
| 7 | 0.1 | Yes | No | 0.25% Na-metabisulfite |

All components of the GS-101 solution were added in the order given above. After the addition of each component, ultrapure water was added until the component was fully dissolved, before proceeding to the addition of the next component. The pH was checked and adjusted to 7.0 using 10% NaOH, if necessary. Finally, ultrapure water was added until a total weight of 10 grams was achieved, and these GS-101 formulations were filtered twice using a sterile Acrodisc 0.2 μm filter unit. This filtration step was carried out in a laminar flow cabinet, as the following steps.

Ultimately, for each of the 7 formulations of Table 1, 32 grams of the sterile bulk emulsion were weighted and 8 grams of the respective sterile GS-101 solutions were added. All mixes were homogenized by shaking vigorously.

GS-101 formulation #3 was also aerated with Na gas for 90 minutes to get rid of all oxygen that might be present in the sample. In this way, the effect of the presence of oxygen on the stability of the GS-101 (i.e., the amount of air oxidation) could be investigated by making a comparison with GS-101 formulation #2.

Incubation of the GS-101 Sterile Emulsions

All GS-101 sterile emulsions were stored overnight at 5° C. The next day, 6 aliquots of each emulsion, of approximately 4 grams each, were placed in climatic rooms for stability testing.

The GS-101 sterile emulsion formulations were incubated at 25° C./60% RH (relative humidity) or 40° C./75% RH for different time periods. Analysis were carried out as described below on day 0 (T0), 1 week (T1w) and 2 weeks (T2w).

RP-HPLC

The percentage assay, i.e., the ratio of purities (intact GS-101 oligonucleotides) versus impurities (degraded GS-101 oligonucleotides), expressed as a percentage, was calculated for each GS-101 sterile emulsions, using chromatographic conditions summarized in Table 2 below.

TABLE 2

| HPLC system | Waters Acquity H-Class or equivalent |
|---|---|
| Data-acquisition system | Waters Empower 3 or equivalent |
| Column | Water Acquity UPLC OST BEH C18 2.1 mm ID × 50 mm, 1.7 μm particle size |
| Mobile phase | A: Water<br>B: 17.2 mM triethylamine, 200 mM hexafluoroisopropanol in water<br>C: MeOH |

| | Gradient elution | | | |
|---|---|---|---|---|
| Min | 0.0 | 15.0 | 15.1 | 23.0 |

| Elution mode | % A | 35 | 30 | 35 | 35 |
|---|---|---|---|---|---|
| | % B | 50 | 50 | 50 | 50 |
| | % C | 15 | 20 | 15 | 15 |

| Analytical run time | 15 minutes |
|---|---|
| Total run time | 23 minutes |
| Flow rate | 0.3 mL/minute |
| Injection volume | 20 μL (1 μg of GS-101) |
| Column temperature | 50 ± 3° C. |
| Sample temperature | 10 ± 5° C. |
| Detection | UV detection with analytical (10 mm) flow cell, at λ = 260 nm |
| Purge solvent | Water |
| Needle wash solvent | MeOH |

Results

Addition of Phosphate Buffer Improves the Stability of GS-101

The RP-HPLC percentage assay results of the 7 different formulations are shown in Table 3 below (in %), at day 0 (T0) at 5° C., and after 1 week (T1w) and 2 weeks (T2w) at 25° C. and 40° C. The evolution of the stability is also reported, as the difference of percentage assay result between T1w and T0 (ΔT1w-T0) and between T2w and T0 (ΔT2w-T0). Data have not been standardized and it will appear clearly to the skilled artisan that values remaining within ±5% can be considered comparable values, based on measurement and dilution bias.

TABLE 3

| | | T1 w | | T2 w | | ΔT1 w − T0 | | ΔT2 w − T0 | |
|---|---|---|---|---|---|---|---|---|---|
| Formulation | T0 5° C. | 25° C. 60% RH | 40° C. 75% RH | 25° C. 60% RH | 40° C. 75% RH | 25° C. 60% RH | 40° C. 75% RH | 25° C. 60% RH | 40° C. 75% RH |
| 1 | 91.5 | 82.9 | 62.6 | 82.7 | 49.5 | −8.6 | −28.9 | −8.8 | −42.0 |
| 2 | 92.4 | 93.0 | 82.9 | 91.0 | 79.1 | +0.6 | −9.5 | −1.4 | −13.3 |
| 3 | 97.8 | 97.7 | 87.0 | 95.2 | 80.6 | −0.1 | −10.8 | −2.6 | −17.2 |
| 4 | 98.3 | 96.9 | 90.7 | 97.4 | 88.5 | −1.4 | −7.6 | −0.9 | −9.8 |
| 5 | 97.1 | 96.4 | 89.7 | 95.4 | 89.0 | −0.7 | −7.4 | −1.7 | −8.1 |
| 6 | 92.9 | 89.1 | 70.1 | 87.3 | 62.8 | −3.8 | −22.8 | −5.6 | −30.1 |
| 7 | 99.9 | 93.0 | 77.1 | 90.6 | 65.8 | −6.9 | −22.8 | −9.3 | −34.1 |

The values for assay of all formulations decrease over time and is more pronounced for the samples kept at 40° C./75% RH.

However, it is clear that formulation #1, without phosphate buffer, shows a much greater decrease in assay than the other formulations (−28.9% after 1 week, −42.0% after 2 weeks). Formulations #6 and #7 were made with a phosphate buffer and metabisulfite as an antioxidant, and show a similar decrease (−22.8% after 1 week, −30.1% to −34.1% after 2 weeks), even though formulation #2 and #3 show less of a decrease and don't contain an antioxidant. This means that metabisulfite, which does not comprise a thiol group, is not a suitable antioxidant for this formulation.

On the other hand, formulations #4 and #5, comprising a phosphate buffer and NAC as an antioxidant, show a decrease of less than 10% at 40° C., after a 2-week incubation.

The same can be concluded for the samples kept at 25° C., which shows a slightly decreased stability over time, however insignificant (less than 2% over 2 weeks) in formulations #4 and #5.

Conclusion

These results show the stabilizing effect of agents comprising a thiol group as antioxidant, compared to agents which do no comprise a thiol group, on the degradation of the phosphorothioate oligonucleotide of the composition.

The addition of 15 mM phosphate buffer further improves the stability of GS-101 on a short-term.

Example 2

Long-Term Stability Study

A long-term stability study of GS-101 was initiated and is reported in this example. The emulsion containing 0.86 mg GS-101/g emulsion was evaluated in 5 different formulations, comprising phosphate and/or an agent comprising a thiol group. These formulations were kept at different storage conditions, and the stability of GS-101 in the different formulations was evaluated by RP-HPLC, as described in Example 1.

Materials and Methods

Preparation of the GS-101 Sterile Emulsions

The GS-101 sterile emulsions were prepared similarly to the emulsions of Example 1. These emulsions can contain one or more of the following substances:

0.1% w/w* or 0.25% w/w* of N-acetylcysteine (NAC);
0.436% w/w* of $Na_2HPO_4.12H_2O$ and 0.039% w/w* of $NaH_2PO_4.H_2O$ (15 mM phosphate final in the total composition);
0.086% w/w* of GS-101 having the sequence SEQ ID NO: 2 (5'-TCTCCGGAGGGCTCGCCATGCTGCT-3').

* Percentages are Given in w/w of the Total Composition.

The various composition formulations are detailed in Table 4 below.

TABLE 4

| Formulation number | % of Carbopol ® 980NF (w/w) | 15 mM phosphate buffer? | % of antioxidant (w/w) |
|---|---|---|---|
| 1 | 0.05 | No | No |
| 2 | 0.1 | Yes | No |
| 3 | 0.1 | Yes | 0.1% NAC |
| 4 | 0.1 | Yes | 0.25% NAC |

TABLE 4-continued

| Formulation number | % of Carbopol ® 980NF (w/w) | 15 mM phosphate buffer? | % of antioxidant (w/w) |
|---|---|---|---|
| 5 (Placebo emulsion GS-101-free) | 0.1 | Yes | 0.25% NAC |

Incubation of the GS-101 Sterile Emulsions

The GS-101 sterile emulsion formulations were incubated at 5° C., 25° C./60% RH or 40° C./75% RH for different time periods. Analysis were carried out on day 0 (T0), 2 weeks (T2w), one month (T1m), 2 months (T2m), 3 months (T3m) and 6 months (T6m).

Results

Addition of phosphate buffer together with an agent comprising a thiol group improves the stability of GS-101

The RP-HPLC assay results of the 5 different formulations are shown in Table 5 below (in %), and in FIGS. 3A-C.

TABLE 5

|  |  | T0 | T2 w | T1 m | T2 m | T3 m | T6 m |
|---|---|---|---|---|---|---|---|
| 5° C. | Formulation 1 | 95.6 | — | 91.6 | 87.3 | 82.7 | 75.6 |
|  | Formulation 2 | 95.0 | — | 91.0 | 94.2 | 87.1 | 79.6 |
|  | Formulation 3 | 93.7 | — | 93.5 | 94.8 | 93.9 | 92.1 |
|  | Formulation 4 | 94.6 | — | 93.8 | 98.4 | 95.3 | 95.0 |
|  | Formulation 5 | 0.1 | — | 0.0 | 0.0 | 0.0 | 0 |
| 25° C./60% RH | Formulation 1 | 95.6 | 86.2 | 74.8 | 68.1 | 56.3 | 35.7 |
|  | Formulation 2 | 95.0 | 93.5 | 86.8 | 80.7 | 80.2 | 72.1 |
|  | Formulation 3 | 93.7 | 95.7 | 92.0 | 94.6 | 90.3 | 88.0 |
|  | Formulation 4 | 94.6 | 96.6 | 93.9 | 94.5 | 91.5 | 85.2 |
|  | Formulation 5 | 0.1 | 0.0 | 0.0 | 0.0 | 0.0 | 0 |
| 40° C./75% RH | Formulation 1 | 95.6 | 55.9 | 26.9 | 5.6 | 2.2 | — |
|  | Formulation 2 | 95.0 | 85.0 | 73.9 | 64.4 | 62.0 | — |
|  | Formulation 3 | 93.7 | 92.8 | 86.1 | 86.4 | 77.9 | — |
|  | Formulation 4 | 94.6 | 95.0 | 88.9 | 88.3 | 81.2 | — |
|  | Formulation 5 | 0.1 | 0.0 | 0.0 | 0.0 | 0.0 | — |

These results clearly show a major drop of stability of formulation #1 (without phosphate buffer nor NAC), even at 5° C., when compared to the other formulations.

In comparison, formulation #2, which comprises a phosphate buffer, shows a stabilization of GS-101 and a slowed-down decrease.

Formulations #3 and #4, which comprise a phosphate buffer and NAC as an antioxidant at different concentrations (0.1 and 0.25% w/w final), show further stabilization of GS-101 when kept at 5° C. or 25° C. even after 6 months of incubation.

Unlike the assays of Example 1 which showed no difference in the stabilization of GS-101 with the two NAC concentrations at short-term, long-term studies tend to show an increased stability using higher amounts of antioxidant (0.25% w/w final).

Conclusion

These results confirm the stabilizing effect of 15 mM phosphate buffer on GS-101 at medium- to long-term.

Further addition of an agent comprising a thiol group, such as N-acetylcysteine, offers an even greater stability of GS-101, even after several months of incubation at room temperature or 40° C.

At 4° C., 15 mM phosphate buffer and 0.25% w/w final of N-acetylcysteine fully preserve the integrity of the phosphorothioate oligonucleotide, even after several months.

The invention claimed is:

1. A composition comprising:
a phosphorothioate oligonucleotide and at least one fatty acid and/or at least one emulsifying agent, wherein said composition is sterile and wherein said composition further comprises at least one phosphate compound and at least one agent comprising a thiol group.

2. The composition according to claim 1, being an ophthalmic composition.

3. The composition according to claim 1, wherein the composition is an emulsion.

4. The composition according to claim 1, being an oil-in-water emulsion or a water-in-oil-in-water emulsion.

5. The composition according to claim 1, wherein the agent comprising a thiol group is selected from the group comprising N-acetylcysteine, lipoic acid, DL-cysteine, creatinine, glutathione, 2-mercapto-5-benzimidazole salts, 2-mercaptoethanesulfonic acid salts, Na-edetate, Na-bisulfite and Na-sulfite.

6. The composition according to claim 1, wherein the phosphate compound is selected from the group comprising $Na_2HPO_4$, $NaH_2PO_4$, $Na_3PO_4$, $K_2HPO_4$, $K_3PO_4$, $KH_2PO_4$, $(NH_4)_2HPO_4$, $(NH_4)_3PO_4$, $Mg(H_2PO_4)_2$, $Mg_3(PO_4)_2$, $MgHPO_4$, $MgNH_4PO_4$, $Ca(H_2PO_4)_2$, $CaHPO_4$, $Ca_3(PO_4)_2$, $Ca_8(HPO_4)_2(PO_4)_4$, $H_3PO_4$ and phosphate acid/base conjugate pairs selected from the group comprising $NaH_2PO_4/Na_2HPO_4$, $KH_2PO_4/K_2HPO_4$, $Na_2HPO_4/Na_3PO_4$, and $K_2HPO_4/K_3PO_4$.

7. The composition according to claim 1, wherein the phosphorothioate oligonucleotide is selected from the group comprising antisense oligonucleotides, siRNAs, shRNAs, ribozymes, aptamers, molecular decoys and RNA-DNA hybrid molecules.

8. The composition according to claim 1, wherein said phosphorothioate oligonucleotide is an antisense oligonucleotide.

9. The composition according to claim 1, wherein the phosphorothioate oligonucleotide is an antisense oligonucleotide specific for IRS-1 (insulin receptor substrate-1).

10. The composition according to claim 9, wherein the IRS-1 antisense phosphorothioate oligonucleotide comprises a sequence of at least 12 contiguous nucleotides of SEQ ID NO: 1.

11. The composition according to claim 9, wherein the IRS-1 antisense phosphorothioate oligonucleotide is SEQ ID NO: 2 or a function-conservative derivative thereof, wherein function-conservative derivative of SEQ ID NO: 2 comprises from 9 to 50 nucleotides, has at least about 75% identity compared to SEQ ID NO: 2 and conserves the capacity of inhibiting IRS-1 expression as SEQ ID NO: 2.

12. The composition according to claim 11, wherein said function-conservative derivative of SEQ ID NO: 2 is selected from SEQ ID NO: 3 to SEQ ID NO: 28.

13. The composition according to claim 1, wherein the phosphorothioate oligonucleotide is stable for at least 1 day at 25° C., and/or wherein the phosphorothioate oligonucleotide is stable for at least 1 day at 40° C.

14. The composition according to claim 1, being a pharmaceutical composition and comprising at least one pharmaceutically acceptable excipient.

* * * * *